United States Patent
Pedrazzini

(10) Patent No.: US 8,322,510 B2
(45) Date of Patent: Dec. 4, 2012

(54) SYSTEM FOR AUTOMATICALLY IDENTIFYING, CONVEYING AND ADDRESSING BIOLOGICAL MATERIAL SPECIMENS

(75) Inventor: Gianandrea Pedrazzini, Paradiso (CH)

(73) Assignee: Inpeco IP Ltd., Valletta (MT)

( * ) Notice: Subject to any disclaimer, the term of this patent is extended or adjusted under 35 U.S.C. 154(b) by 239 days.

(21) Appl. No.: 12/745,525

(22) PCT Filed: Nov. 26, 2008

(86) PCT No.: PCT/EP2008/066220
§ 371 (c)(1),
(2), (4) Date: May 28, 2010

(87) PCT Pub. No.: WO2009/068555
PCT Pub. Date: Jun. 4, 2009

(65) Prior Publication Data
US 2010/0300831 A1 Dec. 2, 2010

(30) Foreign Application Priority Data
Nov. 30, 2007 (IT) .............................. MI2007A2254

(51) Int. Cl.
*G01N 35/04* (2006.01)
*G01N 35/02* (2006.01)
(52) U.S. Cl. ..................... 198/346.2; 198/349; 198/599; 198/836.1; 198/370.07; 422/65
(58) Field of Classification Search .................... 422/65; 198/346.1, 346.2, 349, 370.07, 836.1
See application file for complete search history.

(56) References Cited

U.S. PATENT DOCUMENTS

| | | | |
|---|---|---|---|
| 5,351,801 A | 10/1994 | Markin et al. | |
| 5,884,746 A * | 3/1999 | Leisner et al. | 198/346.1 |
| 5,941,366 A | 8/1999 | Quinlan et al. | |
| 6,056,106 A | 5/2000 | van Dyke, Jr. et al. | |

(Continued)

FOREIGN PATENT DOCUMENTS
DE 19621179 A1 11/1997
(Continued)

*Primary Examiner* — Mark A Deuble
(74) *Attorney, Agent, or Firm* — Birch, Stewart, Kolasch & Birch, LLP

(57) ABSTRACT

There is described an automated laboratory system for handling test tubes containing biological material specimens supported by conveying devices (3) along guide lanes (1, 2), in which motorized conveyor belts (62) run, comprising main lanes (1) and secondary lanes (2) for overtaking the conveying devices (3) and/or routing the conveying devices (3) of the test tubes (4) to the various pre-testing, (19-20), testing (17) and post-testing stations (21). Said system further comprises a detecting device (5) of the test tube (4) positioned in the loading area of the test tube (4) into the conveying device (3), a reading device of a barcode applied onto the side surface of said test tube (4) adapted to identify the test tube (4), said barcode being applied to the test tube before it is loaded into the conveyor device, identifying and control means, preferably of the RFID type, of the conveying device (3) of the test tubes (4), comprising a network of antennas (23) appropriately located in the system at stop devices (8) so as to be able to communicate with the transponders of corresponding conveying means (3) storing recognizing data of the corresponding conveying device (3), and a control unit (100) capable of associating the conveying devices (3) of the test tubes (4) to the corresponding test tubes by receiving data and transmitting commands to the devices mounted in the system.

11 Claims, 25 Drawing Sheets

U.S. PATENT DOCUMENTS

| | | | |
|---|---|---|---|
| 6,343,690 B1 | 2/2002 | Britton et al. | |
| 6,458,324 B1 * | 10/2002 | Schinzel | 422/65 |
| 7,112,303 B2 * | 9/2006 | Itoh | 422/72 |
| 7,662,339 B2 * | 2/2010 | Mattila et al. | 422/67 |
| 7,678,331 B2 * | 3/2010 | Shanafelter | 422/65 |
| 7,763,467 B2 * | 7/2010 | Knight | 436/49 |
| 7,858,032 B2 * | 12/2010 | Le Comte et al. | 422/65 |
| 7,939,020 B2 * | 5/2011 | Nogawa et al. | 422/65 |
| 2004/0136869 A1 * | 7/2004 | Itoh | 422/65 |
| 2005/0036907 A1 | 2/2005 | Shoji | |
| 2006/0286619 A1 | 12/2006 | Ricci et al. | |
| 2007/0254277 A1 | 11/2007 | Scrabeck et al. | |

FOREIGN PATENT DOCUMENTS

| | | |
|---|---|---|
| EP | 1106542 A1 | 6/2001 |
| EP | 1505535 A1 | 2/2005 |
| WO | WO 96/25712 A1 | 8/1996 |

* cited by examiner

SYSTEM FOR AUTOMATICALLY IDENTIFYING, CONVEYING AND ADDRESSING BIOLOGICAL MATERIAL SPECIMENS

The present invention relates to a system for automatically identifying, conveying and addressing biological material specimens.

The need for completely automating a production cycle arises from the ever increasing need to ensure reliability, repeatability and safety of the production cycle itself. These objectives are pursued in all industrial fields, including that of laboratory medicine, which is the scope of the present invention.

In order to better elucidate the matter of the invention, the main activities performed in a test laboratory domain are explained, with particular reference to the problems deriving from the low level of automation of biological material specimen management during the testing process of the same.

After having been collected in specific containers, such as, in the case of blood, plastic or glass test tubes, the biological material specimens reach the test laboratory and are subjected to a series of steps aimed at their preparation, testing and subsequent preservation.

Let us see these steps in greater detail:

Step of identifying. The first action to be performed on a biological material specimen is to identify it, i.e. to gather all the information needed for correct specimen testing and reporting. Such an information may be, for example, identification data of the person who supplied the biological material (this ensures the univocal identification thereof, an essential requirement for correct result reporting at the end of the tests), biological material type (blood, urine, saliva, etc.), type of test to be performed on the specimen (this information is needed to define the type of treatment to be performed on the biological material specimen during the step of pre-testing).

Step of pre-testing. The step of biological material specimen pre-testing includes all the actions which must be performed on the specimen in order to prepare it for the step of testing. If the biological material to be treated is blood, these actions consists in centrifuging the sample contained in test tubes and subsequently removing the cap from the same, in order to facilitate the extraction of the biological material from the test tubes during the step of testing.

In some cases, a step of test tube aliquoting is included, in which "daughter" test tubes are created from the main test tube, named "mother" test tube, in which the biological material contained in the mother test tube is distributed.

Step of testing. The step of testing includes the extraction of the biological material specimen from the corresponding container and the actual chemical testing of the specimen. The amount of extracted specimen and the number of tests which are performed depend on the number of tests which must be carried out on the biological specimen.

Step of post-testing. The step of post-testing consists of two main activities: reporting the test results performed during the step of testing on the biological material specimen and preserving the same. In some laboratories, the residual biological material specimen contained in the corresponding container is preserved in refrigerated environments in order to ensure integrity in case of further tests. In order to ensure correct specimen preservation, once the tests have been finished, the container is closed by applying either the original cap or possibly other type of sealing.

Currently, in laboratory medicine, biological material management, divided into the above-described steps, is performed either manually or semi-automatically, the latter generally only in large laboratories.

It is worth emphasizing that the high growth in the demand for laboratory services has implied, over the past twenty years, major technological development in this field; specifically, a trend towards the automation of the single steps characterizing biological material specimen management may indeed be observed.

Let us consider, for example, medium-to-large size laboratories. Such laboratories are nowadays generally provided with specialised machinery for performing the various actions which must be performed on biological materials. For example, we mention devices adapted to centrifuge the specimens and to remove the cap or seal from the biological material containers. During the step of testing, the use of testers is increasingly developing: these instruments are capable of picking an adequate amount of specimen from the container, performing chemical tests on it, and producing and storing the results of the performed tests.

Despite the trend of automazing the single actions of each step, little attention has been devoted to automation of the test process as a whole.

This means that although one may speak of semi-automatic test laboratories in which instruments and devices adapted to perform certain actions on biological material specimens are used, the process however remains strictly dependent on the level of attention and dexterity of the operator when managing the biological material specimens.

The coordination, and sometimes even the performance, of the single actions of the test process is indeed still controlled by the operator, regardless of whether they are either performed manually or even performed by machinery: despite the technological evolution observed during the past years in laboratory medicine, the operator still has the task of performing repetitive and potentially hazardous operations (the latter because they are carried out on biological materials) consisting in picking, conveying, moving, positioning, opening, closing, sampling, and testing containers and corresponding biological material contained therein.

As a consequence of this, it is easy to understand that the main objectives to be pursued in the field of laboratory medicine are the following:

minimising human errors during the biological material specimen test process decreasing the biological risk to which laboratory operators are exposed when handling potentially hazardous biological material specimens (e.g. blood)

speeding up the process, above all considering that thousands of samples are tested everyday in a modern, medium-sized test laboratory.

A system is therefore needed in order to automate the entire working cycle performed on a biological material specimen to be tested, from the first step of identifying the specimen to the collection of the results.

EP-1106542A1 discloses an automated laboratory system comprising a rotational diverting device.

It is the purpose of the present invention to make a system for automatically identifying, conveying and addressing biological material contained in test tubes so as to minimize the human intervention to the greatest possible extent during the various steps of the process, thus decreasing the risks of error and protecting the safety of the operators themselves.

In accordance with the invention, the object is reached by an automated laboratory system as disclosed in claim 1.

A barcode is a string of characters suitable to be read by a barcode reader.

The control unit may be an application software installed on a personal computer, provided with a memory containing all the informations needed for performing the correct activities on the test tubes and adapted to store their lifecycle during the process. The test tube informations includes, for example, personal data of the person from whom the biological material was taken, the tests to be performed on such a biological material, and, in some cases, the level of urgency required for processing the test tube.

The application software installed on the control unit has the capacity of managing urgencies by assigning given priorities to the conveying devices containing the test tubes deemed urgent during the process on the conveying system. Such priorities are made possible also by using appropriate priority and overtaking lanes present in the conveying system.

The devices mounted on the system are connected to the control unit so as to communicate therewith and receive commands in real time.

The stations or modules dedicated to the steps of pre-testing, testing and post-testing physically interface in given positions of the system. Such positions are reachable by the test tubes contained in the conveying devices or carriers and represent the points in which the test tube is processed by the modules.

The modules connected to the system may communicate with the system control unit by means of different communication protocols (serial, TCP/IP. etc.). Such a communication consists in sending information concerning the state of the modules (from the modules to the control unit), and in sending possible executive commands (from the control unit to the modules).

The conveying device or carrier consists in a container, adapted to contain the test tube in vertical, stable position. It moves along the system and may reach all the interfacing positions with the modules. For this purpose, the system employs stop and diverting devices, adapted to stop and divert the conveying devices close to diversions and priority lanes.

The test tube conveying device is identified and checked by transmission of an identification code by a chip contained in the conveying device to a network of antennas arranged along the conveying system.

The test tube is detected by a test tube detecting system which, in addition to detecting its actual presence, also identifies some physical features useful during the subsequent steps of the process. Consequently to confirming the presence of the test tube in the conveying device, the control unit activates the barcode reader which identifies and sends the univocal identification code of the test tube to the control unit.

The association of the test tube and the corresponding conveying device is performed by the control unit after identifying the test tube. This allows to track and check the position of the test tube during all the steps of the process on the system by knowing the identification code of the conveying device which contains it.

These and other features of the present invention will be further explained in the following detailed description of a practical embodiment example shown by way of non-limitative example in the accompanying drawings, in which.

Figure 1:
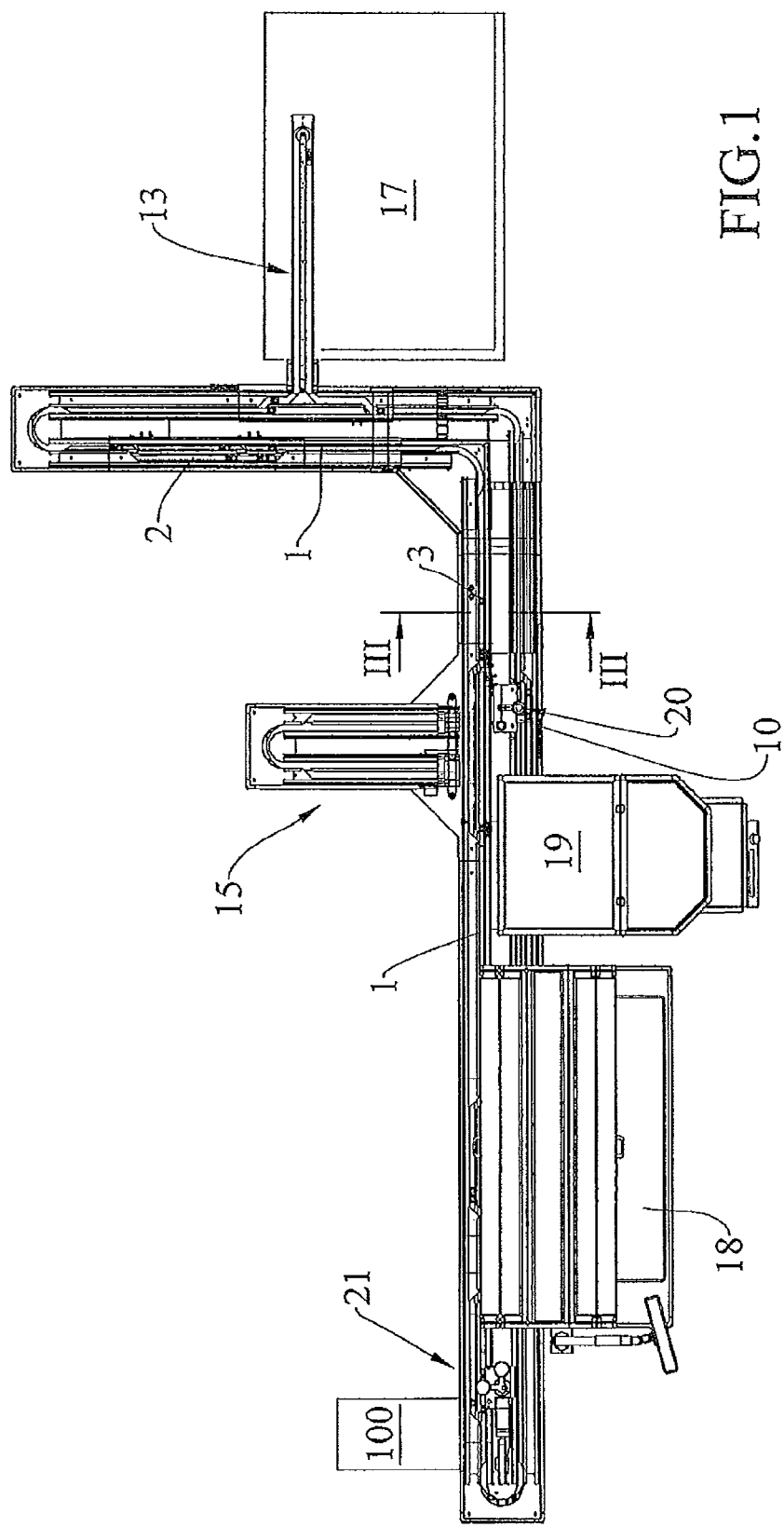
FIG. 1 is a top plan view of the system according to the present invention.

FIG. 1 shows a system according to the present invention comprising main conveying lanes 1 having the function of:
  conveying carriers 3 (i.e. devices adapted for conveying test tubes, as described in international patent application n. PCT/EP2006/067294) containing test tubes 4 or empty carriers 3 to be filled with test tubes 4;
  addressing said carriers 3 to secondary conveying lanes 2, parallel to the main lanes 1 and positioned externally thereto, which allow said carriers 3 to reach or overtake pre-testing modules or stations 19 and 20, testing modules or stations 17 (or testers, instruments adapted to test biological material specimens) and post-testing modules or stations 21. Such modules 17, 19-21, not being the object of the present invention will not be described but only quoted to provide a clearer explanation of the conveying system.

Figure 2:
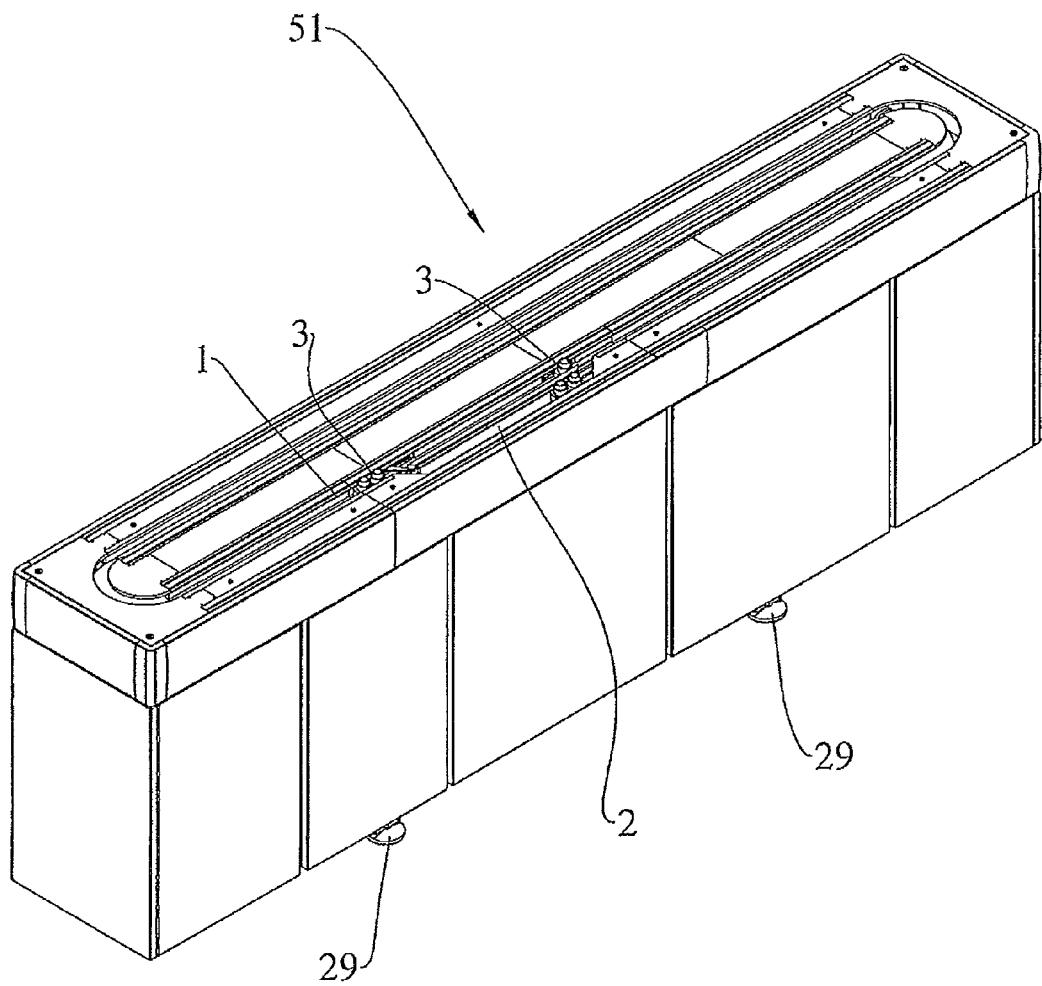
FIG. 2 is a perspective view of a portion of the system.
Figure 3:
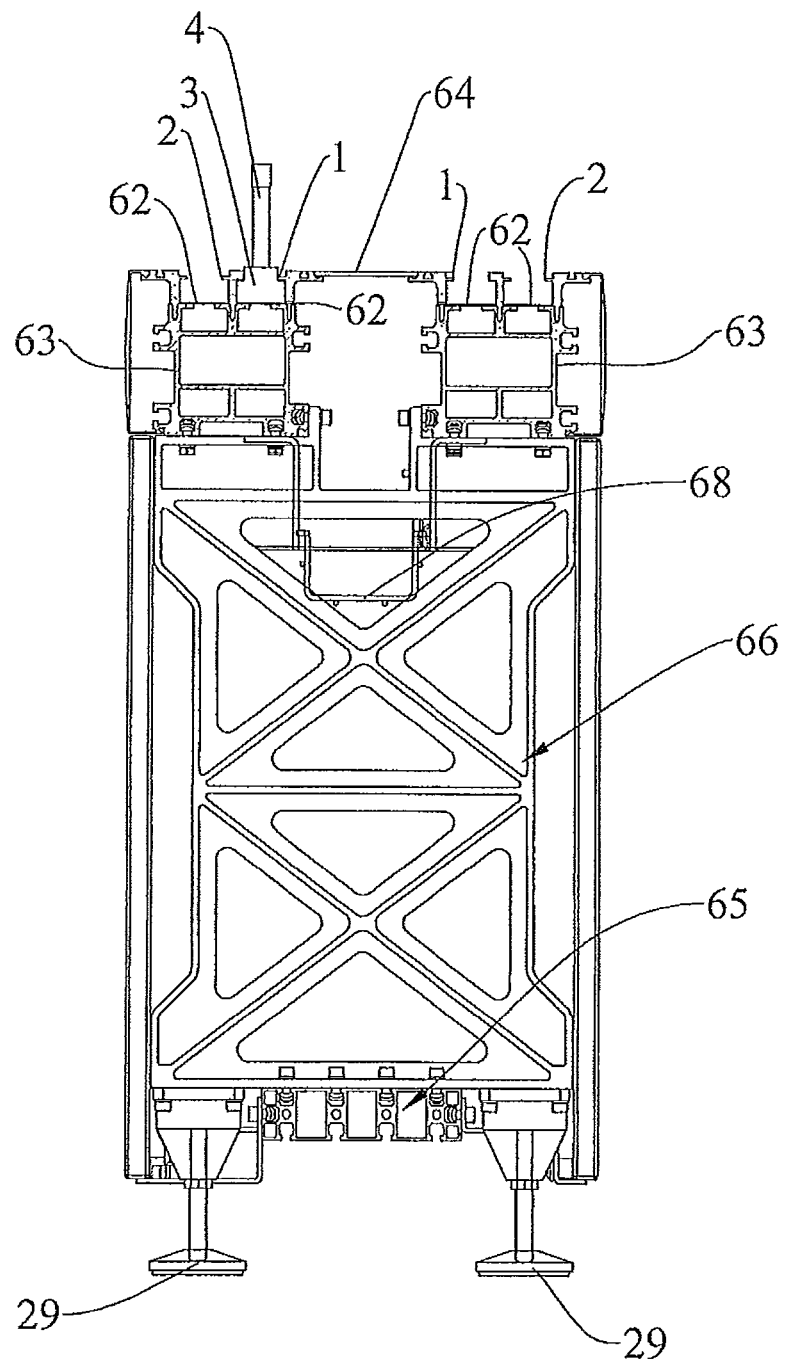
FIG. 3 is a section view taken along the line in FIG. 1.

The reciprocally parallel main 1 and secondary 2 lanes accommodate motorized conveyor belts 62 having the purpose of conveying the carriers 3 (FIGS. 2 and 3). A couple of belts 62, which run in one direction, and a couple of belts 62, which run in the opposite direction (FIGS. 2 and 3) are provided for each straight segment of the system (angular and T-shaped connections, as described below).

The conveying system consists of modules 51 (FIG. 2) which are mutually assembled in a variable number according to different configurations for complying with the various needs of test laboratories using the present invention.

Each module 51, in addition to the two couples of lanes 1-2, comprises a sliding structure 63 of the belt 62, on which an upper guard 64 is mounted (FIG. 3) and which rests on a lower profile 65 by means of an upright 66. The lower profile 65 rests on feet 29 which are adjustable in height. A cable holder structure 68 (FIG. 3) is fixed under the two pairs of lanes 1-2.

The belt 62 consists of reticular polyurethane coated with impregnated fabric which ensures a low friction coefficient with the resting surface of the carrier 3 during the movement.

The conveying belt 62 ends are fused by means of an appropriate fusing tool during the installation of the system after the assembly of the conveying modules 51. This type of fusing ensures a homogenous seam between the two ends of the belt forming the conveyor and prevents oscillations of the test tube 4 contained in the carrier 3 when the carrier encounters the belt seam as it travels in the system.

Some pre-testing 19-20 and post-testing 21 modules exert a downward, vertical pressure on the test tube 4 during a step of the process. For example, the decapper module 20, responsible for removing the cap from the test tube during the step of pre-testing. During decapping, such a module, by operating on the upper part of the test tube 4, exerts a vertical downward compressing action on the test tube 4 contained in the carrier 3. Such a compression is transmitted by the carrier 3 to the belt 62 underneath. Since the carrier 3 is stationary during the step of decapping of the test tube 4, in the operating point of the decapper module 20, the transmitted pressure generates a pinching of the belt 62 between the carrier 3 and the lower part of the structure 63 (which is the sliding surface of the belt). Such a pinching causes the belt 62 to slow down and causes wearing of the supporting base of the carrier 3 on the belt 62 by effect of the rubbing generated by the movement of the belt 62.

The system is provided with a belt lifting device 10 (FIG. 14-17) in order to overcome such a problem.

Figure 14:
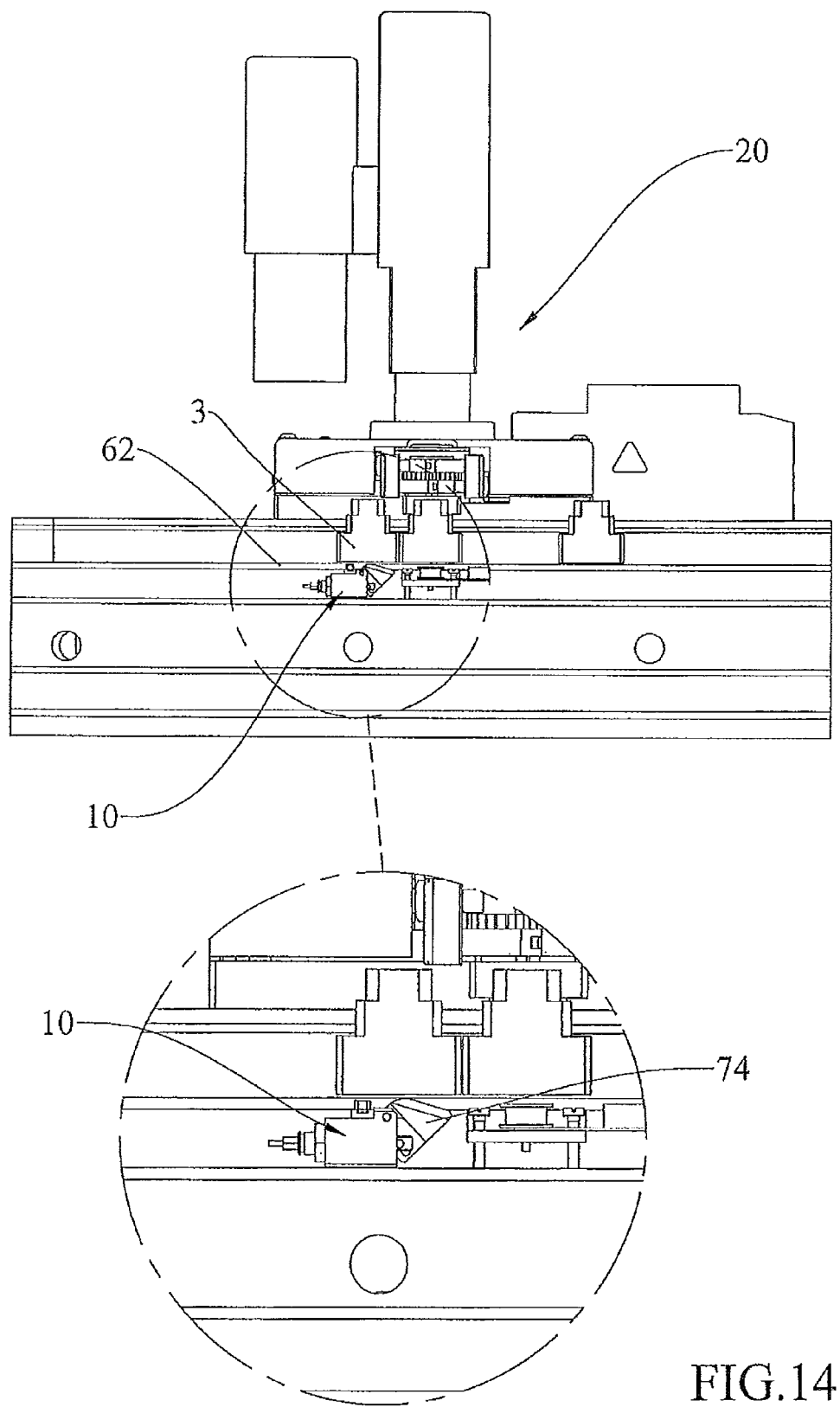
FIG. 14 is a front view of a portion of the system comprising a belt lifting device.
Figure 15:
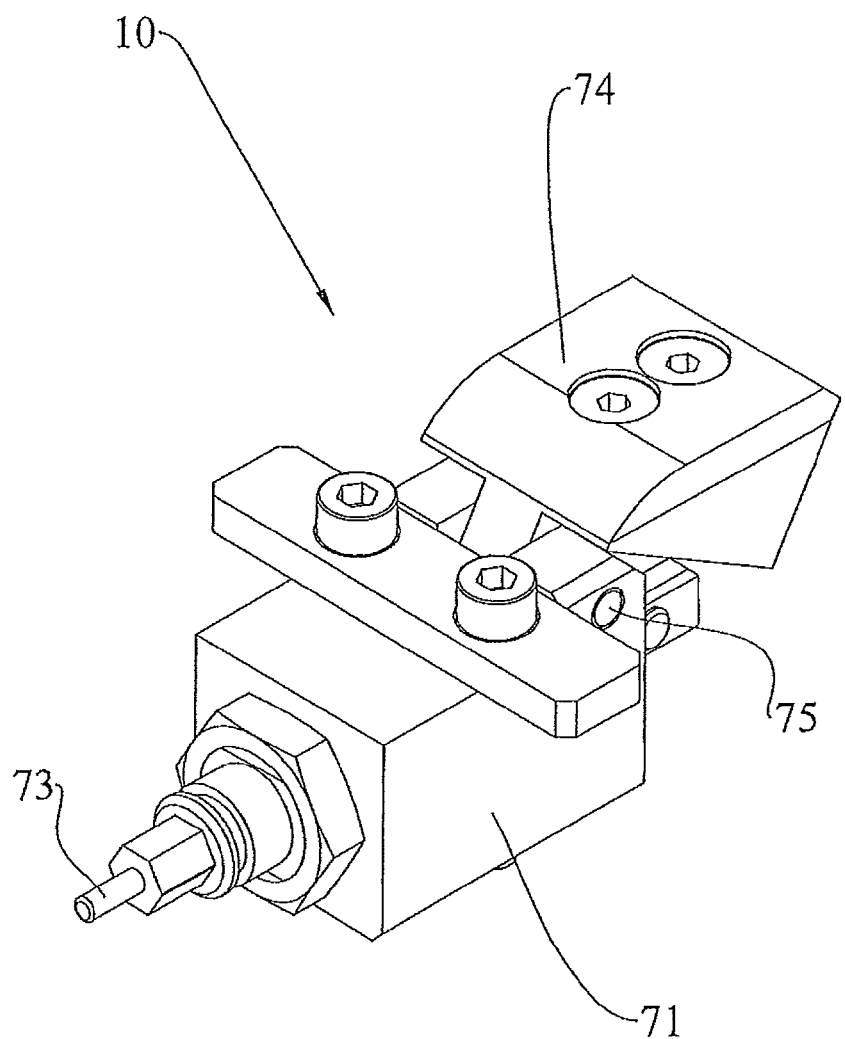
FIG. 15 is a perspective view of the belt lifting device.
Figure 16:
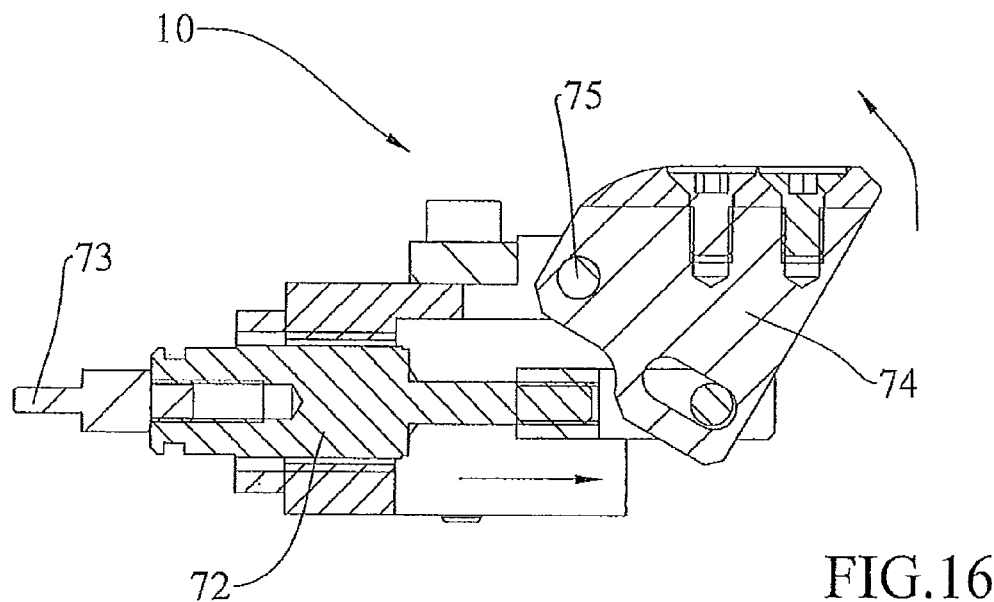
FIG. 16 shows a longitudinal section view of the lifting device in FIG. 15 in resting position.
Figure 17:
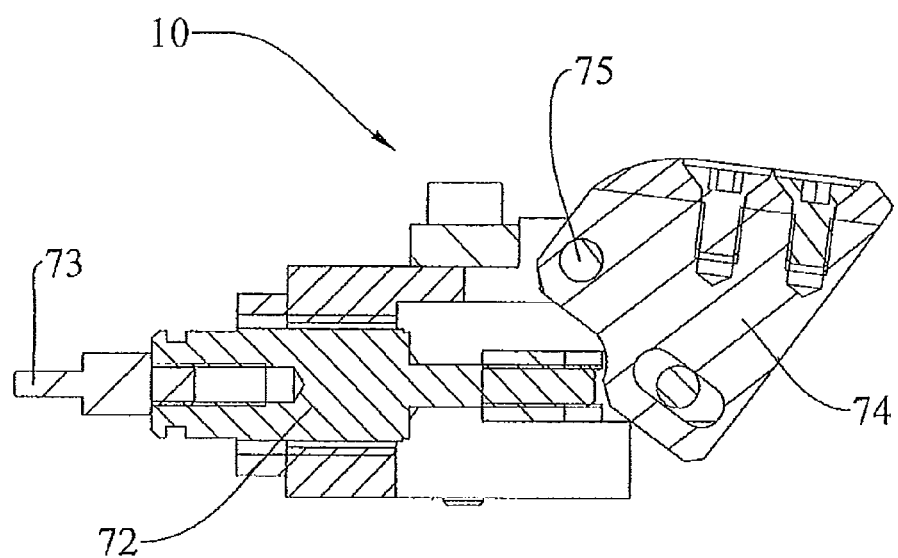
FIG. 17 is a section view similar to that in FIG. 16 with the lifting device in working position.

Said belt lifting device 10 has the function of lifting the belt 62 by approximately 1.5 mm close to the action points of the modules which have the described problem, in order to generate a suspension of the belt 62 in said points. Such a suspension prevents the contact of the belt 62 against the structure 63 (FIG. 14).

Said lifting device 10 consists of an external body 71 containing a pneumatic cylinder 72 fed by means of a flow governor 73. The movement of such a cylinder generates the rotation of a runner 74 about a pin 75. In absence of carrier 3 (resting conditions), the runner 74 is in the lowered position (FIG. 17) and the belt is not raised. When a carrier 3 reaches the operating point of the concerned module, the pneumatic cylinder 72 moves in the direction of the runner, generating a clockwise rotation. Following such a rotation, the runner 74 is arranged in the position shown in FIG. 16 generating the lifting of the belt 62. The presence of a spring (not shown) inside the belt allows the return to horizontal position.

Figure 18:
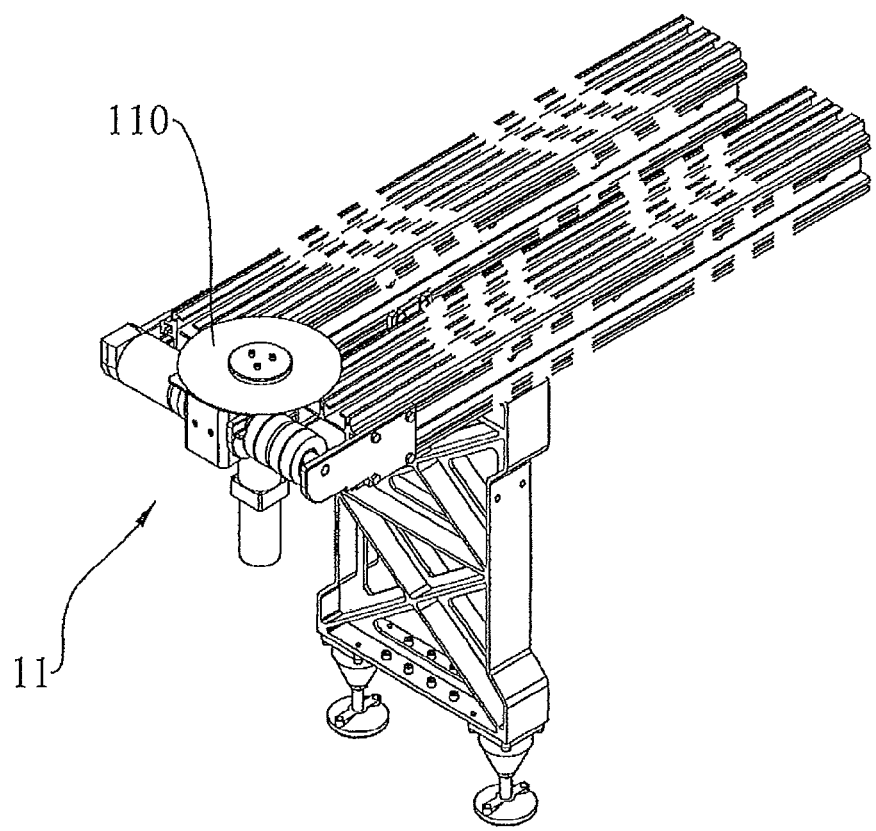
FIG. 18 is a perspective view of a portion of the system with a test tube U-turn device.

A U-turn device 11 (FIGS. 18-19), having the function of transferring the carrier 3 from the couple of belts 62 running in one direction to the couple of belts 62 running in the opposite direction, is found at the end of the conveying system in order to allow the carrier 3 to reverse the direction of motion. Said U-turn device 11 comprises a thin plastic plate 110 mounted on a vertical shaft 112 turned by a motor 113.

Figure 19:
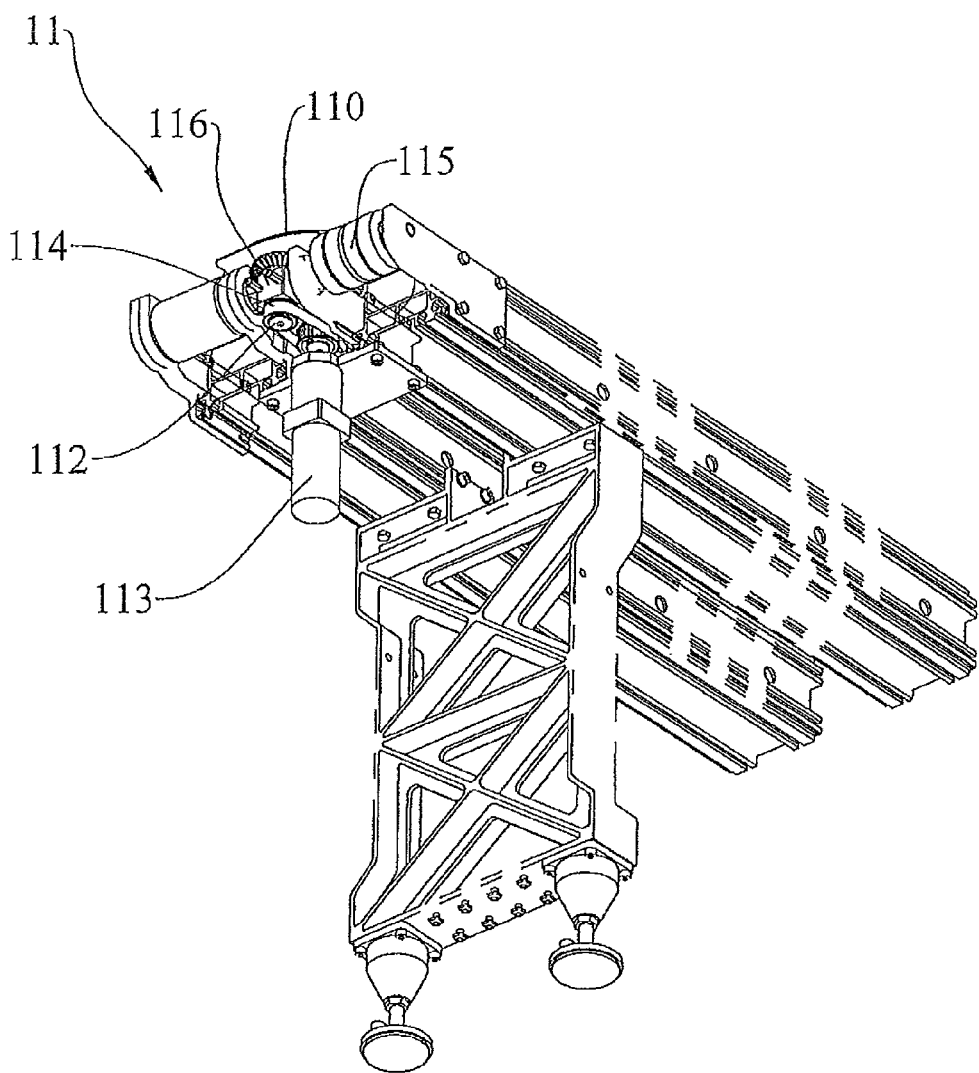
FIG. 19 is a perspective bottom view of the device in FIG. 18.

Said motor 113 is present on each end of the conveying system and in addition to generating the rotation of the plate 110 also has the function of moving one of the two couple of belts 62. Motion is transmitted by means of a belt 114 and an angle transmission 116 to a pulley 115 which, by turning, generates the motion of the couple of belts 62 (FIG. 19).

When the carrier 3 reaches the end of the belt 62, the rotational movement of the plate 110 allows the carrier 3 to go the belt 62 moving in the opposite direction.

Figure 26:
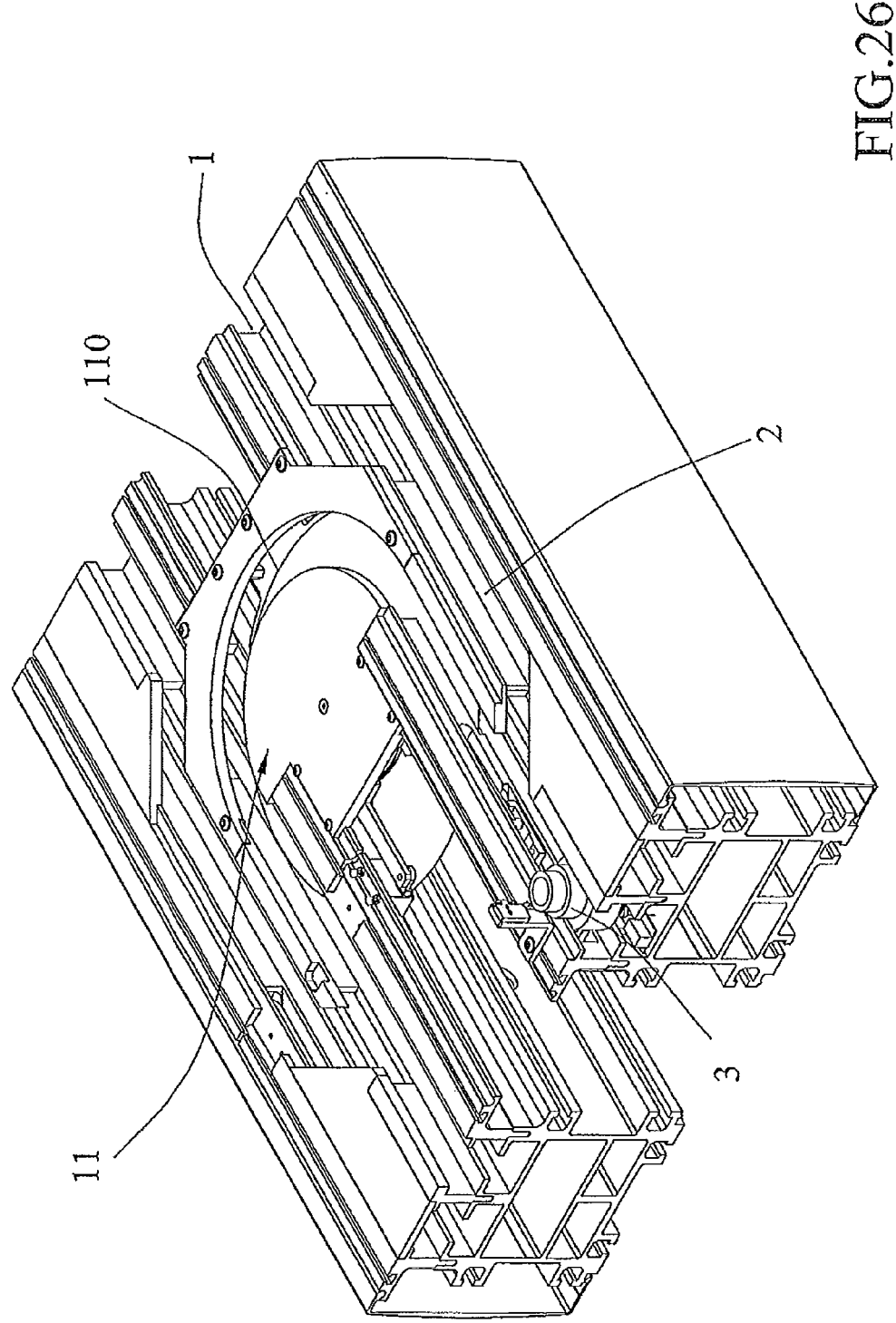
FIG. 26 is a perspective view of a portion of the system comprising a further test tube U-turn device.

Said U-turn device 11 may be present also in an intermediate segment of the conveying system (FIG. 26), in order, when needed, to allow U-turns of empty carriers 3 or carriers containing test tubes which must not be processed by the modules connected to the conveying system subsequent to the point in which the U-turn is present. The presence of U-turns is particularly useful in large-sized conveying systems.

A carrier 3 the direction of which must be inverted proceeds on the main lane 1 and is channeled into the U-turn device 11; if instead the carrier needs to proceed in rectilinear direction along the conveying system it is conveyed onto the secondary lane 2 to overcome the U-turn.

Figure 20:
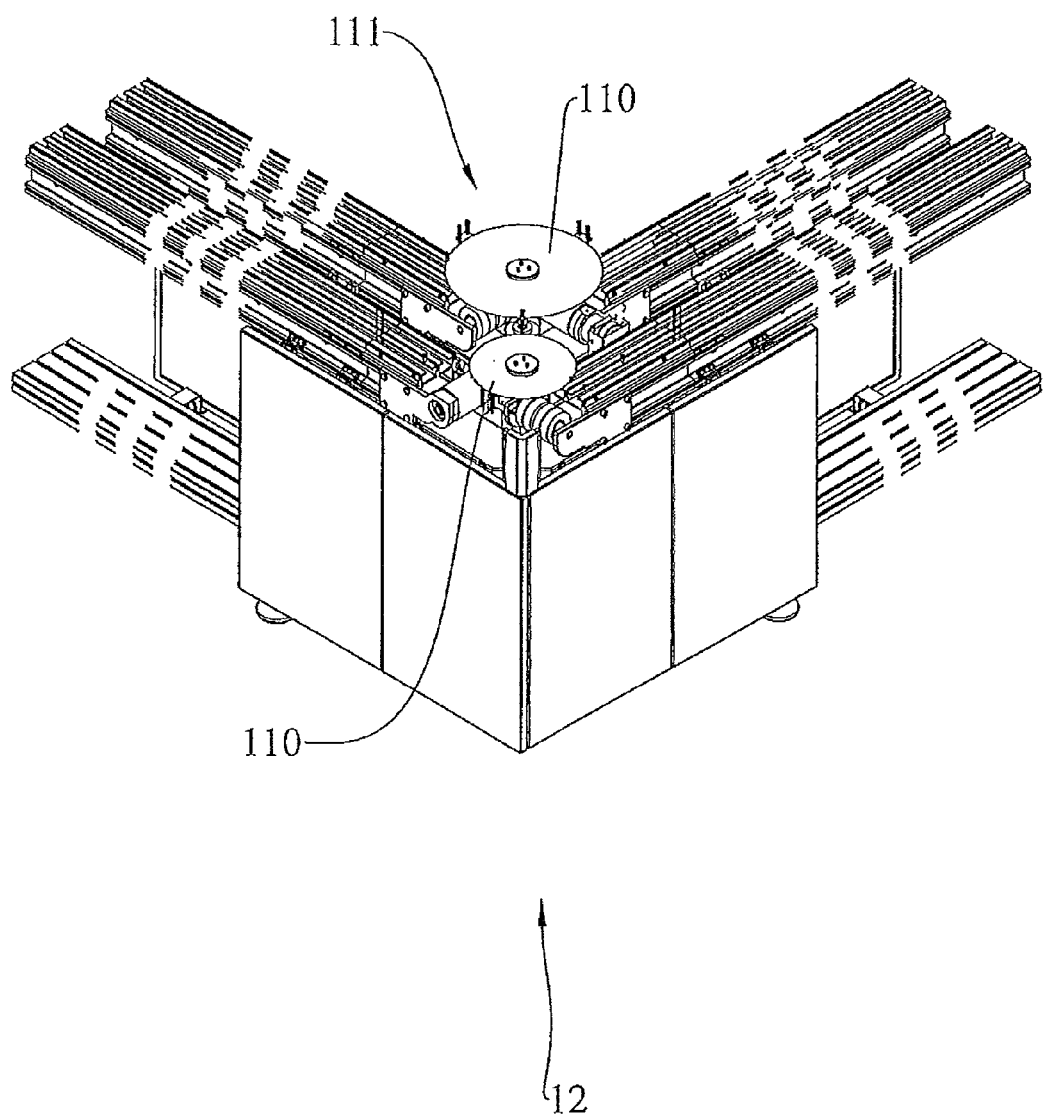
FIG. 20 is a perspective view of an angled portion of the system.
Figure 23:
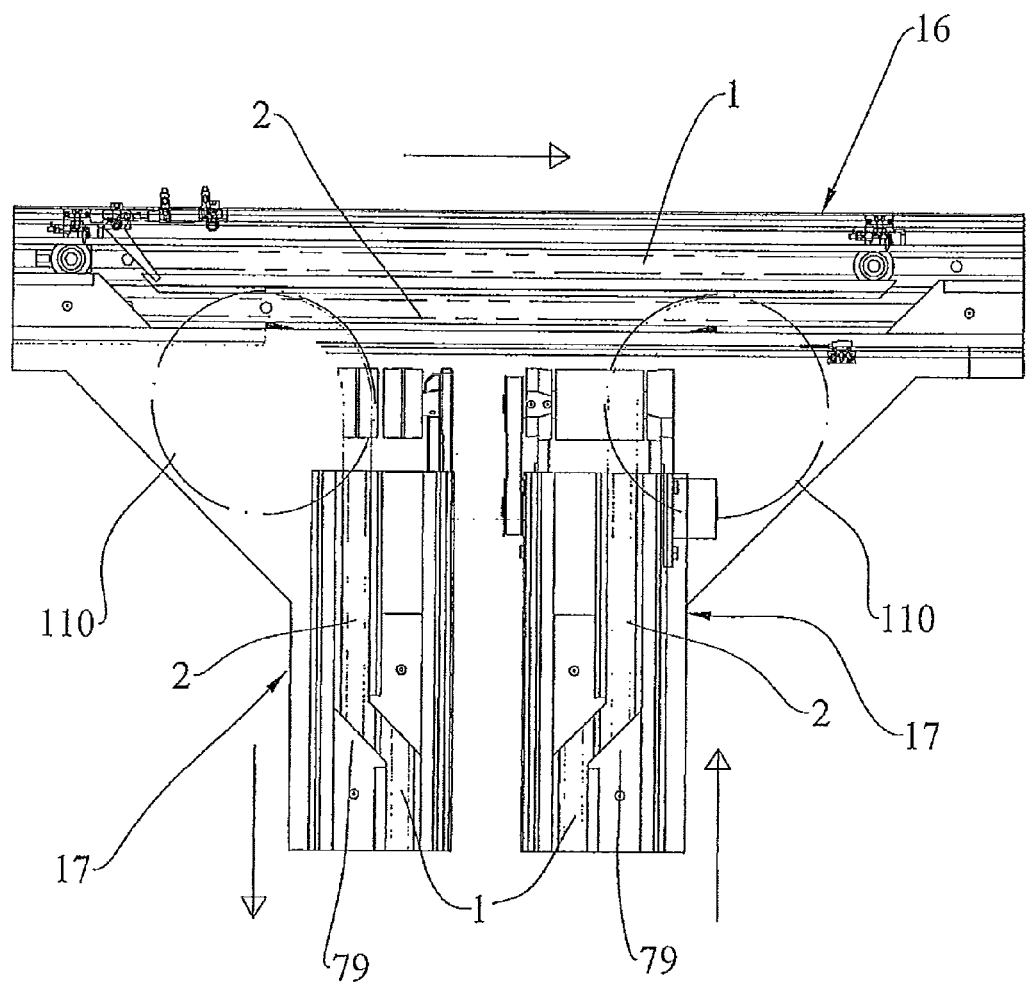
FIG. 23 shows a top plan view of a T-shaped portion of the system.

As mentioned, the conveying system is a modular structure consisting of a varying number of conveying modules 51. These features allows to adapt the conveying system to the various test laboratories in which it is installed, thus complying with the logistic features of such laboratories. This objective is reached also in virtue of the use of the following two modules:

corner module 12 (FIG. 20);

a T-shaped turning module (FIG. 23).

The corner module 12 is used to obtain an angular path of the conveying system. Said angled module may be made according to different angles, e.g. the embodiment herein described is a 90° angle module which confers an L-shape to the conveying system.

FIG. 20 is a perspective view of such a module 12, consisting of the perpendicular intersection of two conveying modules 51. Two direction changing devices 111, entirely similar to the U-turn devices 11 described above, allow the carrier 3 to travel from one conveying module 51 to the other arranged in a perpendicular position. Specifically, the plate 110 in internal position guarantees the passage of the carrier 3 from the main conveying unit 1 to the one in perpendicular direction, while the external plate 110 guarantees the passage of the carrier from the secondary conveying unit 2 to the one in perpendicular direction.

Figure 4:
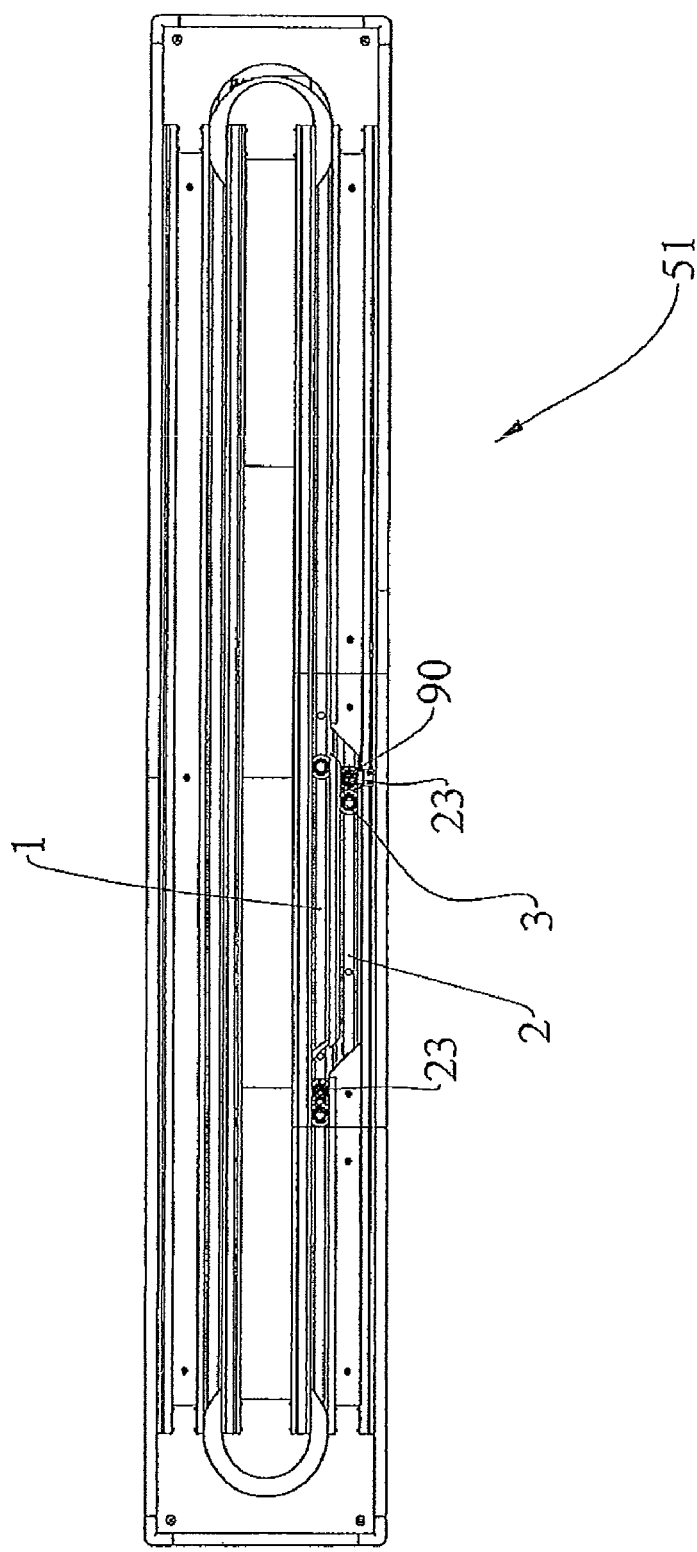
FIG. 4 is a top plan view of the carrier detecting device.
Figure 25:
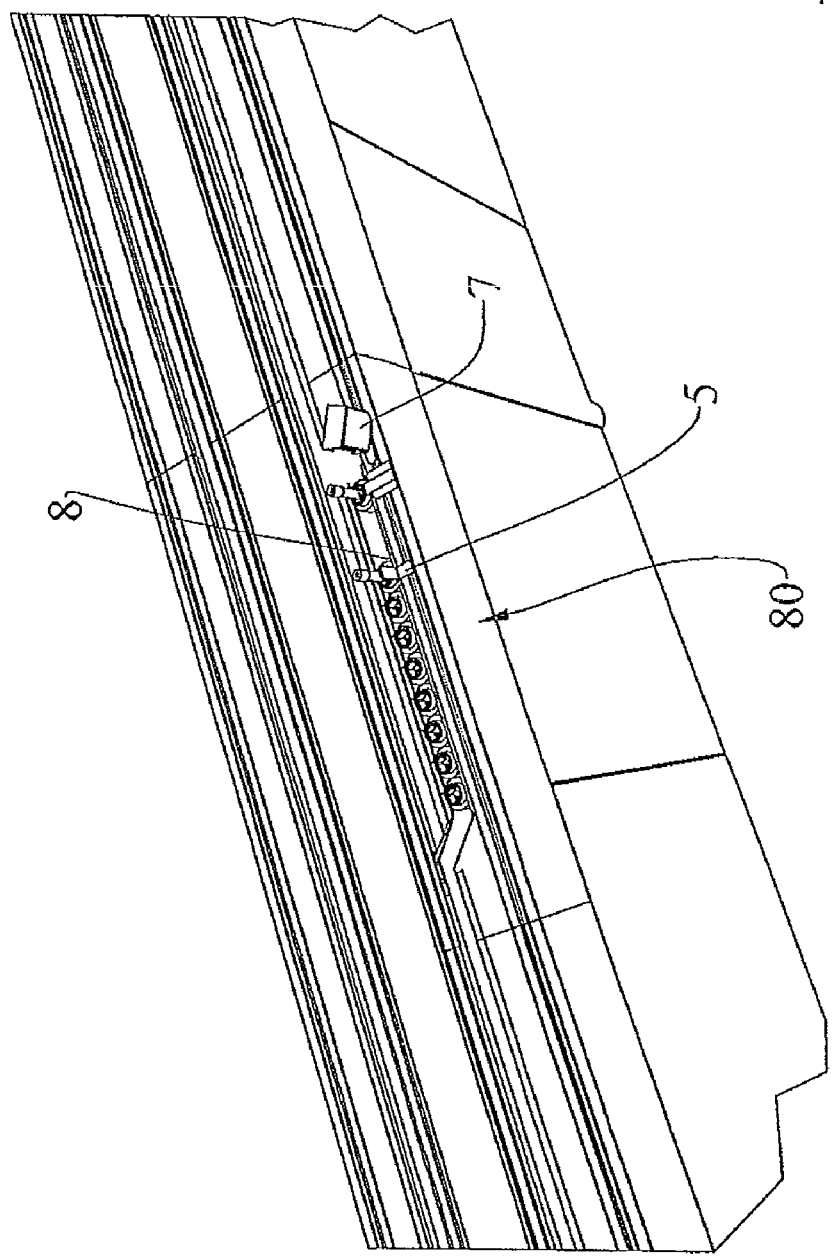
FIG. 25 is a perspective view of a portion of the system including a lane for manually loading urgent test tubes into carriers.

The T-shaped turning module (FIG. 23) comprises two rectilinear segments 16-17 having a "T"-shaped configuration. The segment 16 is joined by the ends to further rectilinear segments of the type shown in FIG. 4 and comprises a main lane 1, in which runs the carrier 3, which is diverted onto the secondary lane 2 of the segment 16, being routed onto the secondary lane 2 of the segment 17 by means of a plate 110. The shape of an upper guard 79 forces the travelling carrier 3 to pass into the main lane 1 of the segment 17 (FIG. 25). The return of the carrier 3 onto the segment 16 of the T-shaped module 15 is equivalent: the carrier 3 is forced by the shape of the upper guard 79 to travel onto the secondary lane 2 of the segment 17, to then be diverted onto the secondary lane 2 of the segment 16 by means of a further plate 110.

In order to track the path and check the right addressing of the conveying system, the position of the moving carrier 3 is recorded by a carrier detecting apparatus. Such a carrier detecting apparatus is capable of identifying the presence and the identity of the carrier 3 in real time as the carrier 3 travels in the conveying system. It is based on radio-frequency identification technology (RFID), and consisting of a network of antennas 23 distributed under the conveying system belt 62

(FIG. 4), which are capable of receiving the data transmitted by a transponder 90 contained in the body of the carrier 3 at the passage of the carrier 3.

Such a transponder 90 is a device provided with an internal memory capable of storing and transmitting data; it does not require electric power because it is powered by the magnetic field generated by the network of antennas 23. At the passage of the carrier 3 on the conveyor belt close to an antenna 23, the electromagnetic field generated by the antenna feeds the transponder, which by modulating such an electromagnetic field, transmits the data stored in its internal memory to such an antenna 23. The identification code which allows to recognize the carrier itself is stored in the memory of a carrier transponder. It is a univocal code, which means that a single, personal identification code is associated to each conveying system carrier 3. The identification code information received by the antenna is sent to the control unit 100, which associates the position of the carrier 3 on the conveying belt, on the basis of the position of the antenna 23 which sent the information. The antennas 23 positioned under the belt 62 are strategically distributed along the conveying system: an antenna 23 is present in each point in which the identity of a carrier 3 must be checked or known, to decide the path and store the lifecycle (e.g. in the diverting points between the main conveying unit 1 and the secondary conveying unit 2, or in the points in which the test tubes 4 are processed by the modules).

Figure 7:
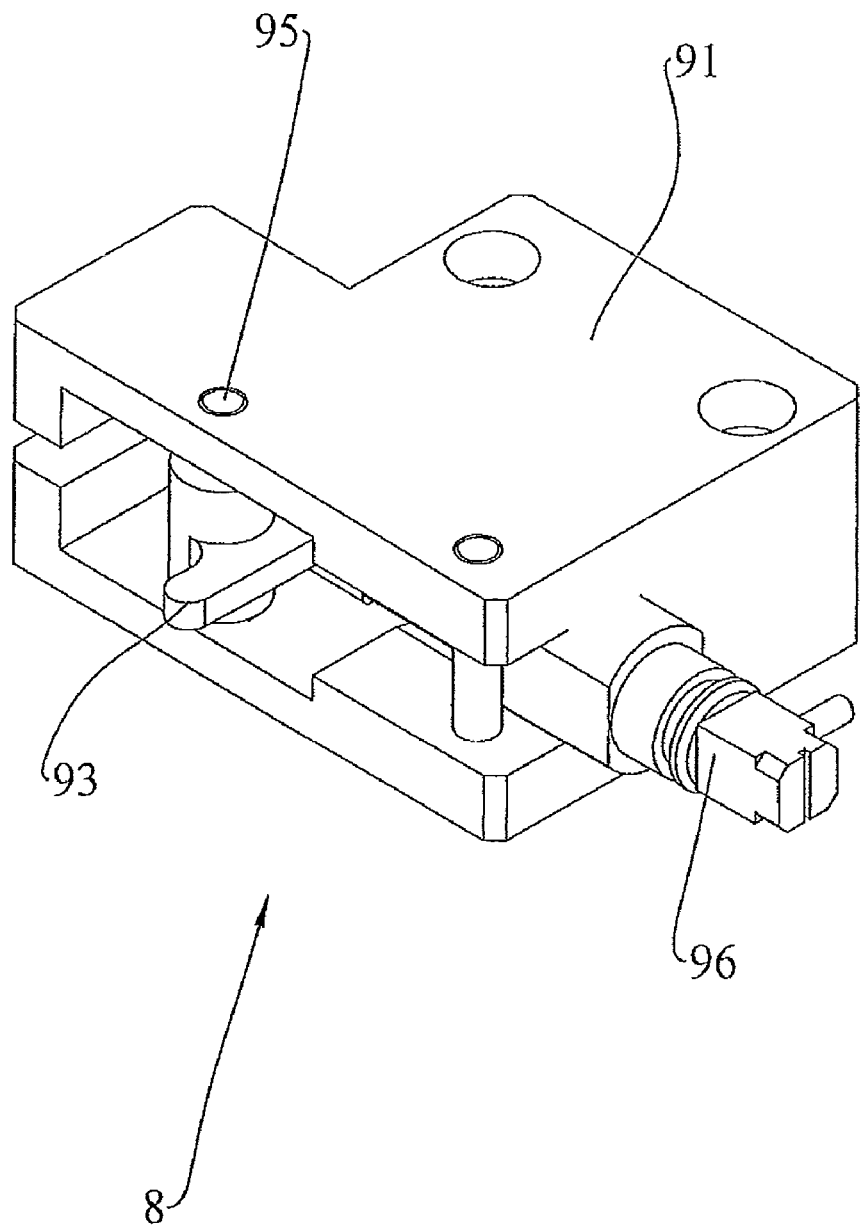
FIG. 7 is a perspective view of a stop gate used to stop the carriers moving on the conveyor belt.
Figure 8:
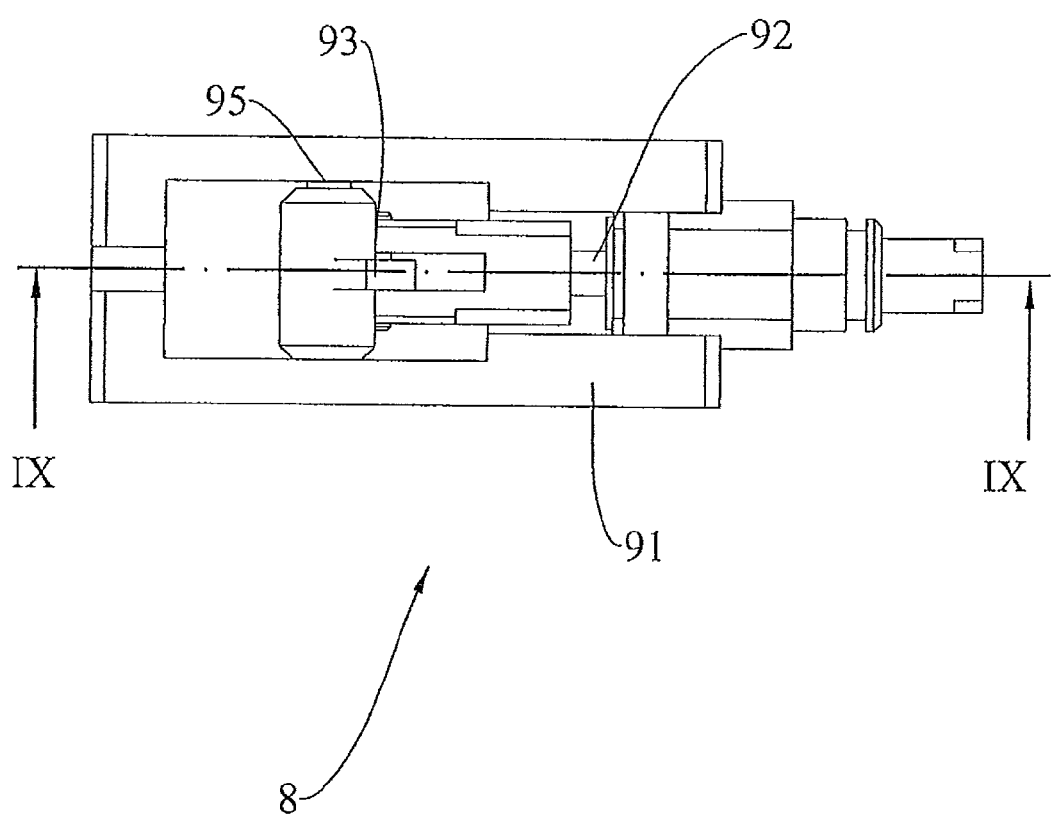
FIG. 8 is a front view of the stop gate.
Figure 9:
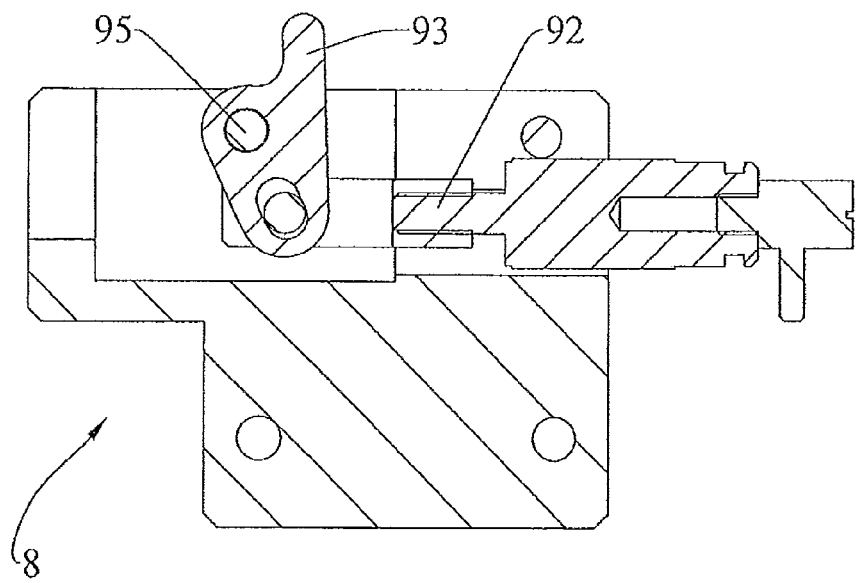
FIG. 9 is a section view taken along line IX-IX in FIG. 8.
Figure 10:
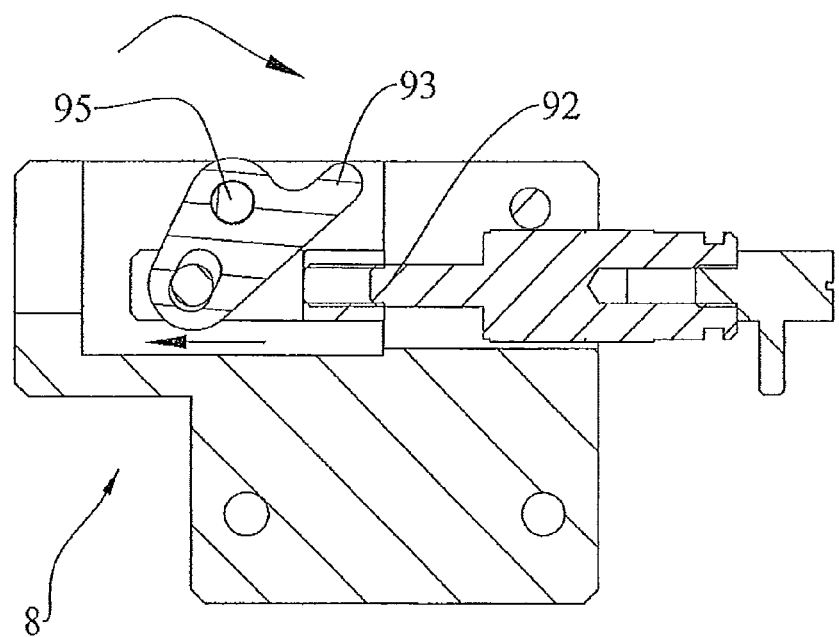
FIG. 10 is a section view similar to that in FIG. 9 with the gate in resting position.
Figure 13:
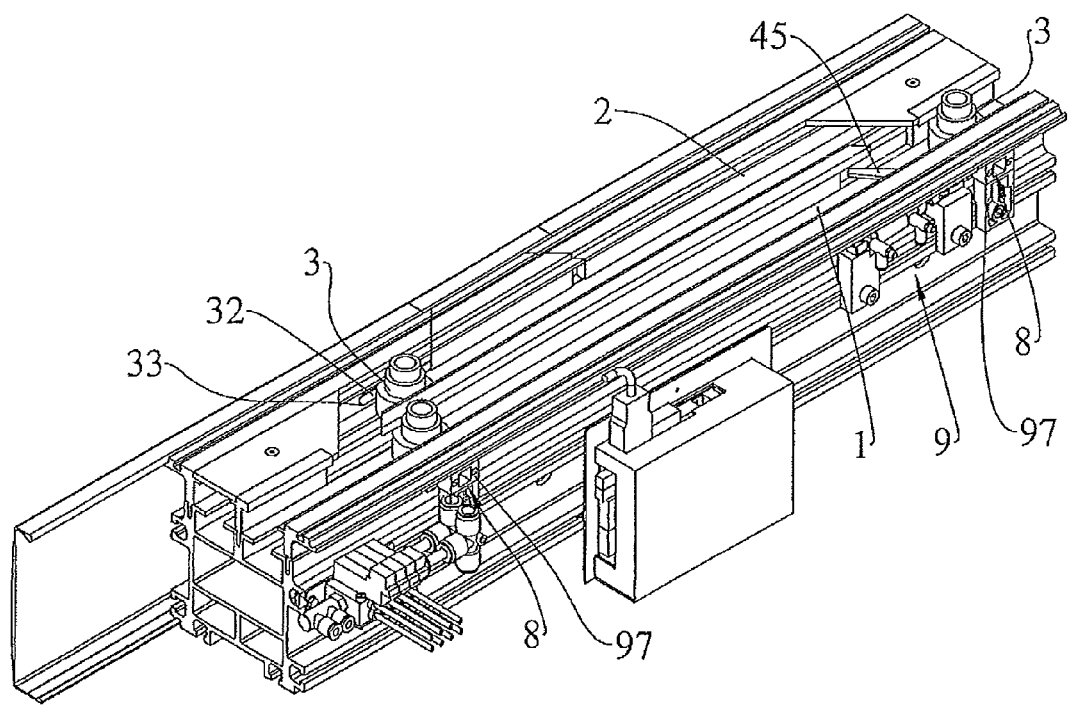
FIG. 13 is a perspective top view of a portion of the system comprising an overtaking lane.

The identification of a carrier 3 by n antenna 23 is made possible by the presence of a stop gate 8 located close to each antenna 23 (FIG. 7-10). The stop gate 8 stops the carrier 3 in the exact point in which the antenna 23 is positioned under the belt 62, allowing the antenna 23 to receive the identification code sent by the transponder 90. Said stop gate 8 consists of an external body 91 fixed to the structure 63 of the supporting module by means of a support 97 (FIGS. 7 and 13). Said external body 91 encloses a selector 93, fixed to the external body by means of a screw inserted in a hole 95. The movement of a pneumatic cylinder 92, fed by a flow governor 96, determines a clockwise rotation of the selector 93 about the pin 95 (FIGS. 9-10). The selector 93 is normally in turned configuration, named "open" position (FIG. 10). In order to stop the passage of a carrier, the selector 93 turns anticlockwise going to the "closed" position (FIG. 9): in such a position, the selector protrudes and blocks the path of the carrier on the conveying system. A spring located inside the selector 93 allows to restore the "open" position. The ID information of the carrier 3 identified by the antenna 23 is communicated to the control unit, which routes the carrier towards the pretesting 19 and 20, testing 17 and post-testing 21 modules, diverting, if needed, its path from a main lane 1 to a secondary lane 2, or to a sampling lane 13.

Figure 11:
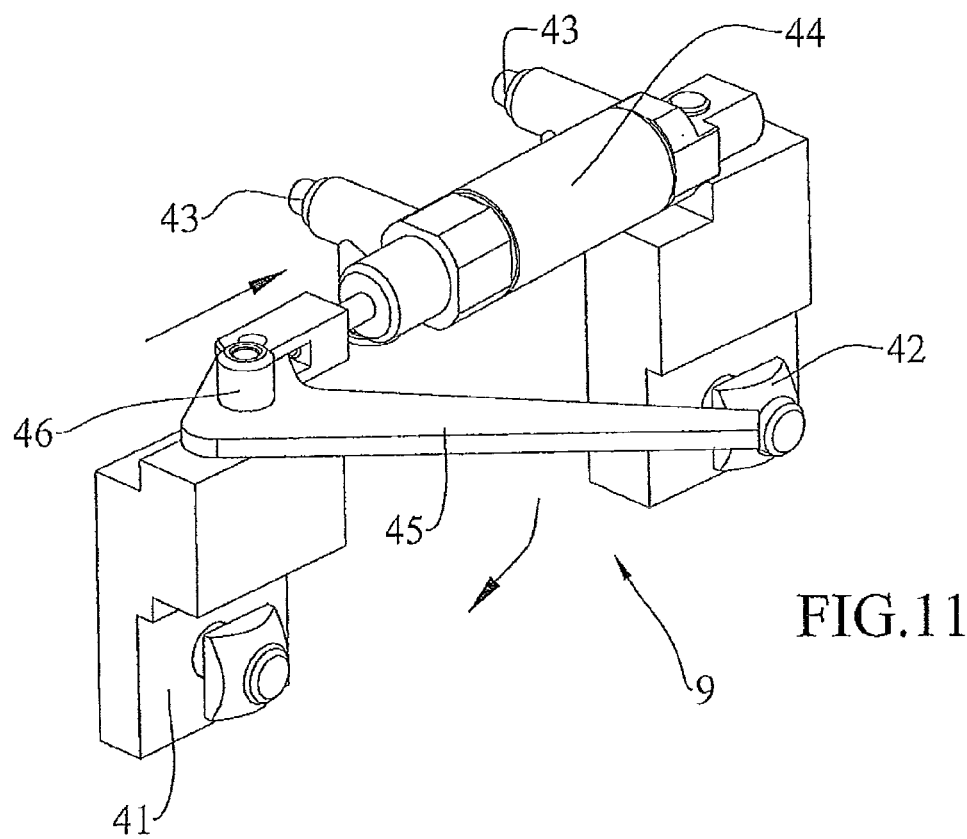
FIG. 11 is a perspective view of a diverting device used to divert the carriers moving on the conveyor belt.
Figure 12:
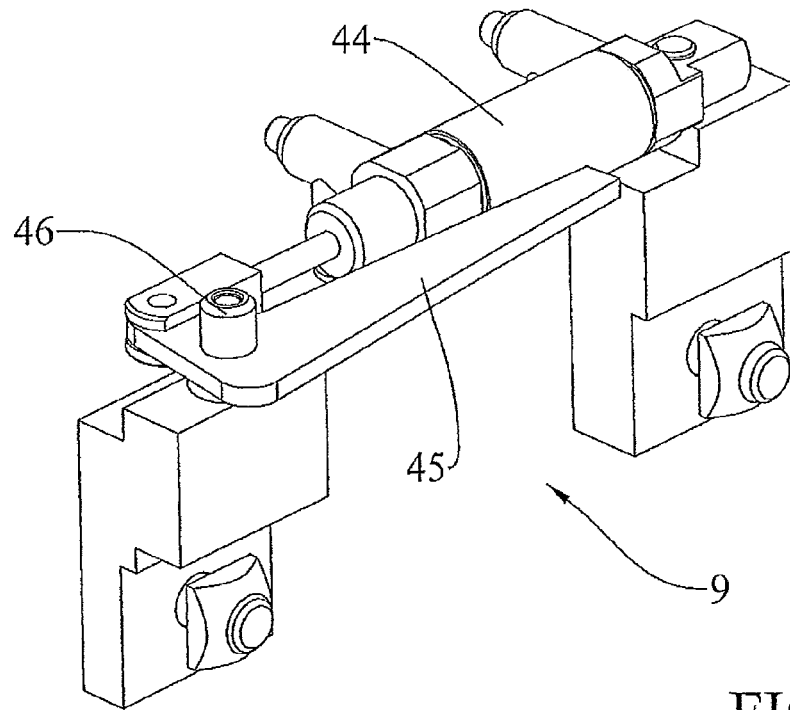
FIG. 12 is a view similar to that of FIG. 11 with the diverter in resting position.

Such a diverter is obtained by means of a carrier diverting device 9 (FIGS. 11-12), installed close to a diversion of the main lane 1 in a position exactly subsequent to that of a stop gate 8 (FIG. 13). Said diverting device 9 consists of a front support 41 and a rear support 42, which allow to fix the carrier diverter device 9 onto the internal side wall of the structure 63 of the main lane 1. Two flow governors 43 adjust the movement of a cylinder 44, responsible for the rotation of a lever 45 about a pin 46. The lever 45 is normally in so-called "open" position: it turns anticlockwise, as shown in FIG. 12, in order to allow the carriers 3 to proceed along the path of the main lane 1. When a carrier 3 needs to be diverted from the main lane 1 to the secondary lane 2, the lever 45 is turned clockwise (FIG. 11). In such a position, named "closed" position, the lever 45 protrudes onto the conveying module, forcing to divert the path of the carrier 3 from the main lane 1 to the secondary lane 2 (FIG. 13).

The secondary lane 2 may have different functions according to how a given module interfaces with the rest of the conveying system.

For modules interfaced with the secondary lane 2 (i.e. in the external position), it has the function of addressing lane of the carriers 3 containing the test tubes 4 to such modules. In this configuration, the position of the diverting device 9 which precedes the diversion is "open", i.e. the carriers 3 are forced to proceed onto the main lane 1. Such a device passes to the "closed" position if the control unit 100 decides to route a carrier 3 in the secondary lane 2.

Figure 5:
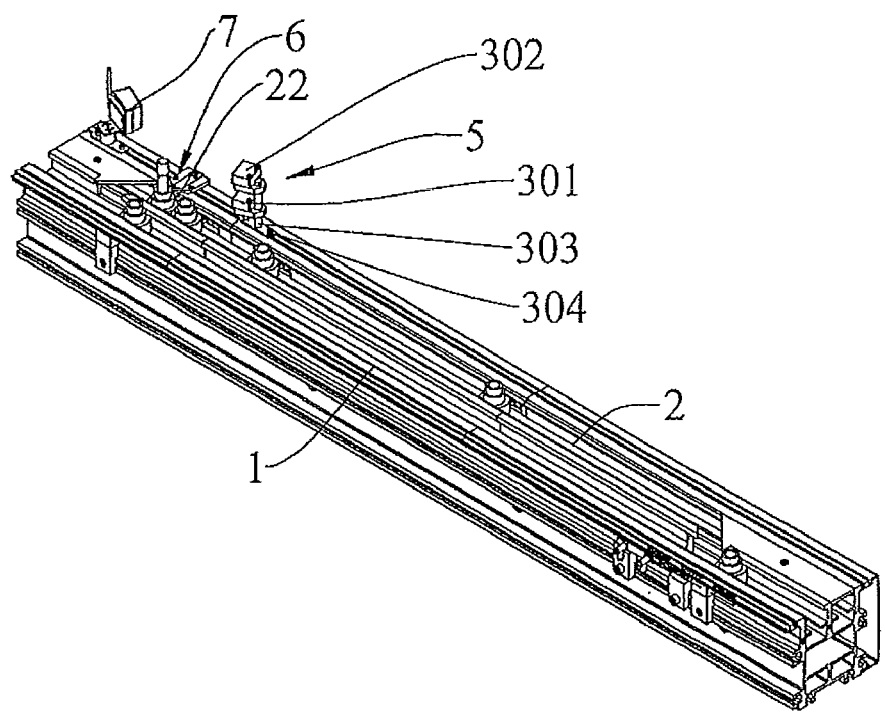
FIG. 5 is a perspective view of a portion of the system with the detecting and identifying point of the test tube in the carrier on a conveyor belt.
Figure 6:
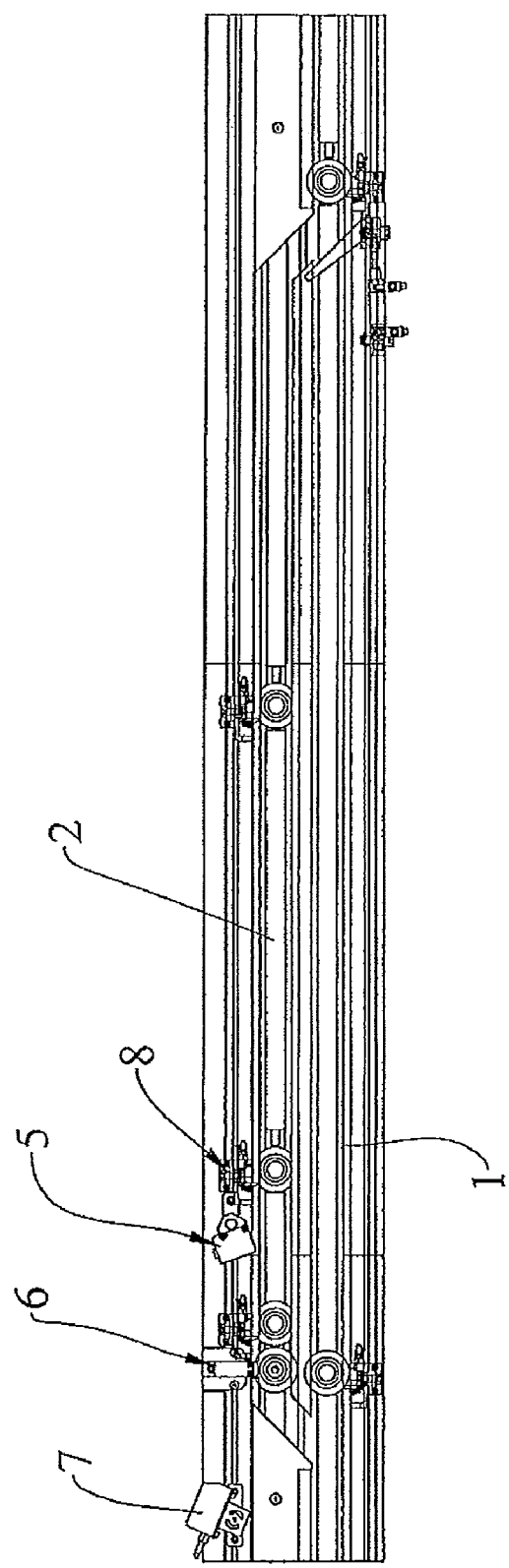
FIG. 6 is a top plan view of the portion in FIG. 5.

For the modules 51, which for design reasons interface with the main lane 1 (FIG. 1) instead of with the secondary lane 2 (i.e. in an internal position, such as, for example, the decapper module 20 and the recapping module 21), the secondary lane 2 has the function of overtaking lane of such modules (FIG. 5).

Consequently, a carrier 3 containing a test tube 4 which does not require the type of processing provided by such modules, or an empty carrier 3 which must overtake such modules, is diverted into said secondary lane 2, to then be routed back onto the main lane 1 at the end of the diversion 62is. In such a configuration, the diverting device 9 which precedes the diversion is in a "closed" position, i.e. in a position so as to force the carriers to enter the secondary lane 2, considered in this case as the main or overtaking lane (FIG. 13). The diverting device 9 passes to the "open" position if the carrier must be routed to the module.

The return to the main lane 1 of the carriers 3 diverted onto the overtake lane is ensured by the presence of a presence sensor 32 positioned inside a window 33 on the side wall of the structure 63, internally facing the overtake lane 2 (FIG. 13). If such a sensor detects the passage of a carrier 3 on the overtake lane 2, the stop gate 8 on the main lane 1 in position adjacent to the sensor 32 remains closed, blocking the passage of a possible carrier 3 and allows to return the carrier 3 from the overtake lane to the main lane 1. Such a procedure ensures a "carrier return" management avoiding potential collisions between carriers on the overtake lane 2 and carried on the main lane 1.

Figure 21:
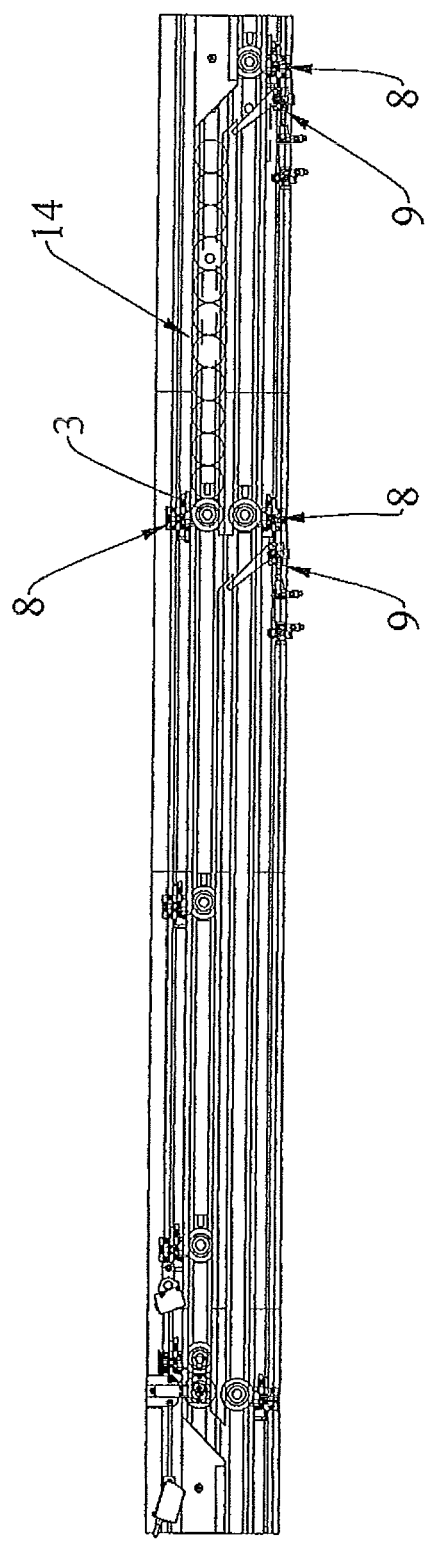
FIG. 21 is a top plan view of a portion of the system with an empty carrier lane for urgent test tubes.

A further use of the secondary lane 2 consists in making an empty carrier lane 14 (FIG. 21), located upstream of the loading/unloading module 18. Said empty carrier lane 14 has the function of ensuring the availability of carriers for loading the test tubes 4. Such a need may arise as consequence of a request of a test tube to be urgently processed in case of non-availability of carriers in the system. In this condition, the control unit 100 may activate the stop gate 8 and release an empty carrier 14 to be loaded with a test tube 4 onto the secondary lane 2.

Alternatively to the described empty carrier lane 14, a manual loading empty carrier lane 80 may located downstream of the loading/unloading module 18 (FIG. 25) in order to ensure the availability of empty carriers in case of urgent test tubes to be loaded in the system. Said lane has a given number of queued empty carriers, as shown in FIG. 25, at the stop gate 8 in the "closed" position. The operator can access such an area present in the system and manually load the queued carriers 3 with urgent test tubes 4. A test tube detecting device 5, by detecting the presence of the test tube, activates the stop gate, taking it to the "open" position allowing the carrier 3 loaded with the test tube 4 to reach the subsequent stop point in which a barcode reader 7 is located. Said barcode reader, as will be explained below, allows to identify the test tube and to associate it to the corresponding carrier, identified by the antenna 23 positioned under the belt.

Figure 22:
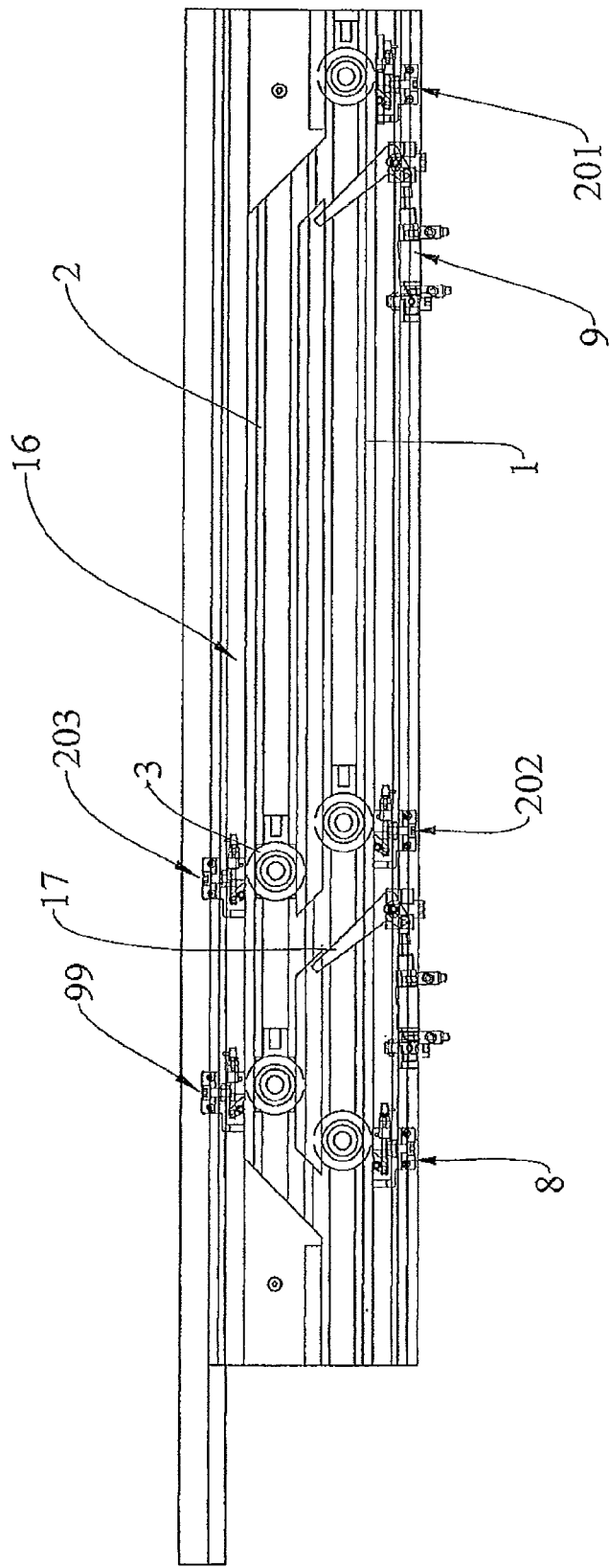
FIG. 22 is a top plan view of a portion of the system with urgent test tubes close to the testers.

The need to guarantee the sampling priority of test tubes deemed urgent is ensured by means of an urgent test tube buffer 16 (FIG. 22) located close to the testers, consisting of a priority diversion 17 located on the main lane 1. The carriers containing urgent test tubes reaching the stop gate 201, to the far right in FIG. 22, are not diverted, but proceed on the main lane 1. At the stop gate 202, the carrier containing an urgent test tube is diverted by means of the diverting device 17 onto the secondary lane 2, towards the sampling point 99. In order to allow such a carrier 3 to have absolute priority, a stop gate 203 located on the secondary conveyor unit 2 controls the travel of carriers 3 containing non-urgent test tubes 4 previously diverted onto the secondary lane 2, thus stopping the travel if a carrier 3 containing an urgent test tube was diverted from the stop gate 202.

A test tube detecting device 5, positioned in the detecting point 22 (FIG. 5) on the secondary lane 2 close to the test tube loading/unloading module 18 (FIG. 1), allows to detect the presence of the test tube 4 and of some of its physical features, such as, for example, in the case of a camera detecting system, the height, diameter and color of the cap. This information may be used by the various modules during the subsequent steps of the process (e.g. diameter information is used by some testers to establish the amount of liquid to be picked from the test tube during the step of testing). The type of physical identified features depends on the type of device used for detecting the test tube.

In the embodiment shown, presence and height detecting devices 5 are used consisting of two photoelectric presence sensors: the presence sensor 301 and the height sensor 302. Said sensors 301 and 302 are activated by the control unit 100 when the antenna 23 positioned under the belt close to the detecting point 22 detect the identification code of the carrier 3, which is maintained stopped in the position by the stop gate 8. The presence sensor 301 is activated to check the presence of the test tube 4 in the carrier 3, while the height sensor 302 is activated to check the height of the test tube. Said sensor 302 is positioned so as to detect the test tube only if this has a height contained in a given range of heights. In the case in which the test tube is lower than the minimum value of such a range, the sensor 302 does not detect its presence and the test tube is considered "low" if it has a height such as to be included in the scanning window of the sensor 302 it is considered "high".

The two sensors 301 and 302 are installed on a support 303 fixed to the upper guard 304 of the system.

Following the confirmation of test tube presence sent by the detecting device 5 to the control unit 100 (along with the information on test tube height), a bar code reader 7 (FIG. 5) is activated to identify the bar code present on the label applied to the side wall of the test tube 4. In order to allow a correct reading of the barcode, a test tube rotation device 6 ensures a rotation of the test tube on its axis during the laser scanning time of said barcode 7, as described in international patent application n. PCT/EP2006/069275.

A barcode reader is a laser device capable of scanning the barcode. The barcode of the test tube 4, once decoded into an identification code, is communicated to the control unit 100.

The control unit guarantees the univocal association of the identification code of the test tube 4 to the identification code of the carrier 3 identified by the antenna 23 in the detecting point 22. In this manner, it is possible to identify the test tube 4 by means of the corresponding carrier 3 along the process on the conveying system.

After positively completing the identification of the test tube 4, the carrier 3 containing the test tube 4 may start travelling in the system.

The carriers 3 containing test tubes 4 which must reach a tester 17 and allow test tube sampling, are derived onto the secondary lane 2, to then by diverted a second time onto a sampling lane 13. Different sampling lane configurations may be made (plate, straight, L-shaped) in accordance with the different types of existing testers 17.

When a testing module 17 is reached, the test tube contained in the carrier 3 is stopped at the working point of said module, where the biological material may be picked. Such a picking may be performed from closed test tubes and from open test tubes, on the basis of the tester type, and is generally performed by means of either needles, if the test tube is closed, or pipettes, if the test tube is open, actuated by mechanical arms having the task of aspirating the biological material from the test tube and conveying it into the tester.

If the tester uses needles, the test tube must not be torn before reaching in the tester, because the needle is inserted into the test tube through the rubber present on the upper surface of the cap.

If the tester uses pipettes, the test tube must reach the working point of the tester without cap to allow the pipette to be inserted inside the body of the test tube and to aspirate the specimen.

Unlike the first procedure, this second aspiration procedure does not have particular problems, because in the first case it may not be possible to extract the needle, once it is inserted inside the test tube, thus remaining jammed into the rubber of the cap. Such an error represents a major cause of risk because the test tube could be extracted from the carrier 3 which contains it and lifted by the robotic arm to which the needle is connected and thus carried into the tester, causing damage which is easily imaginable.

Figure 28:
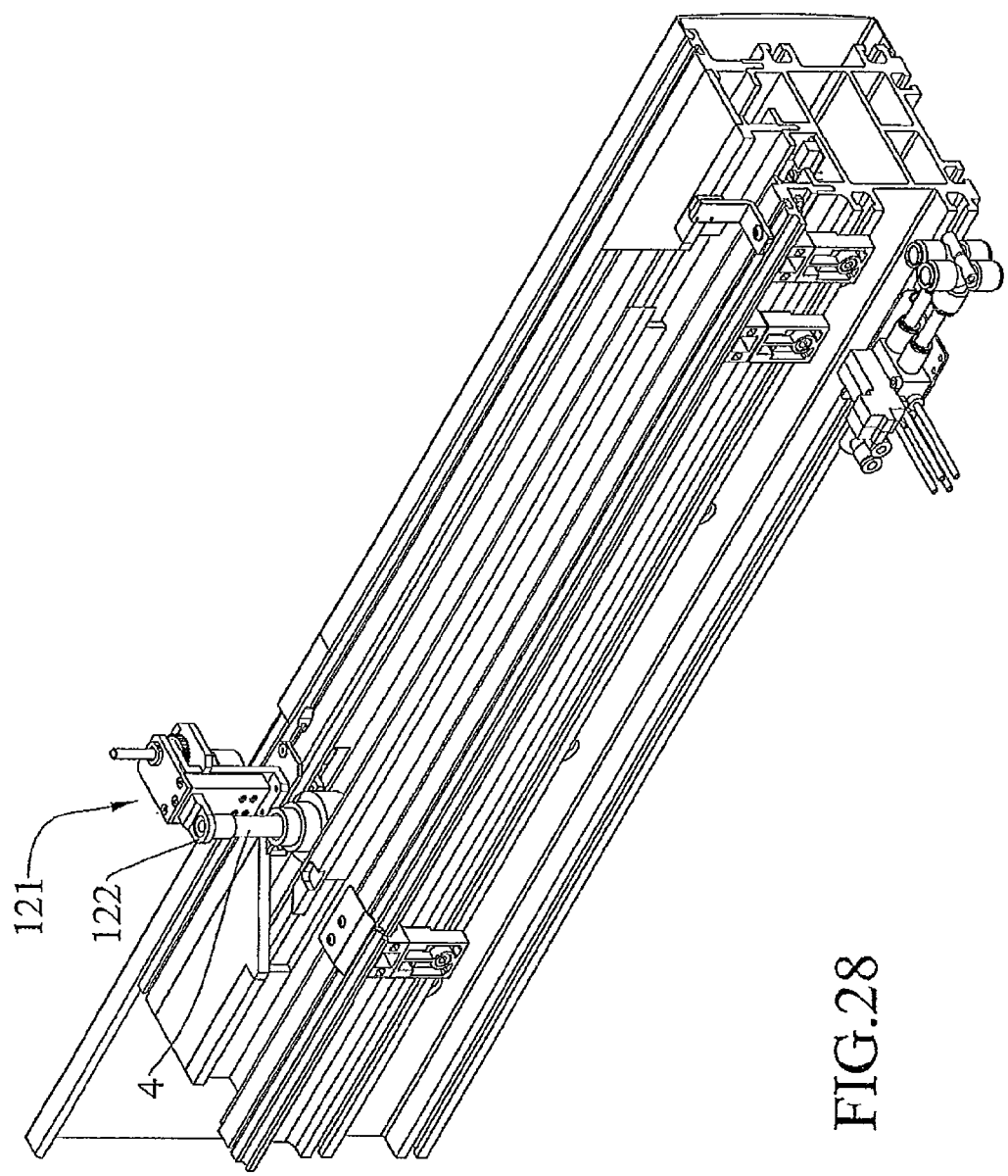
FIG. 28 shows a perspective view of a system portion comprising a device for blocking the test tube in a sampling position, in blocking position.

In order to overcome this problem, a test tube blocking device 121 may be present, adapted to block the test tube contained in the carrier 3 during the step of sampling, as shown in FIG. 28. Said blocking device 121 is mounted on the upper guard 64 of the conveying system and comprises a blocking ring 122 adapted to perform a vertical movement with respect to the surface from the top downwards, and vice versa.

Figure 27:
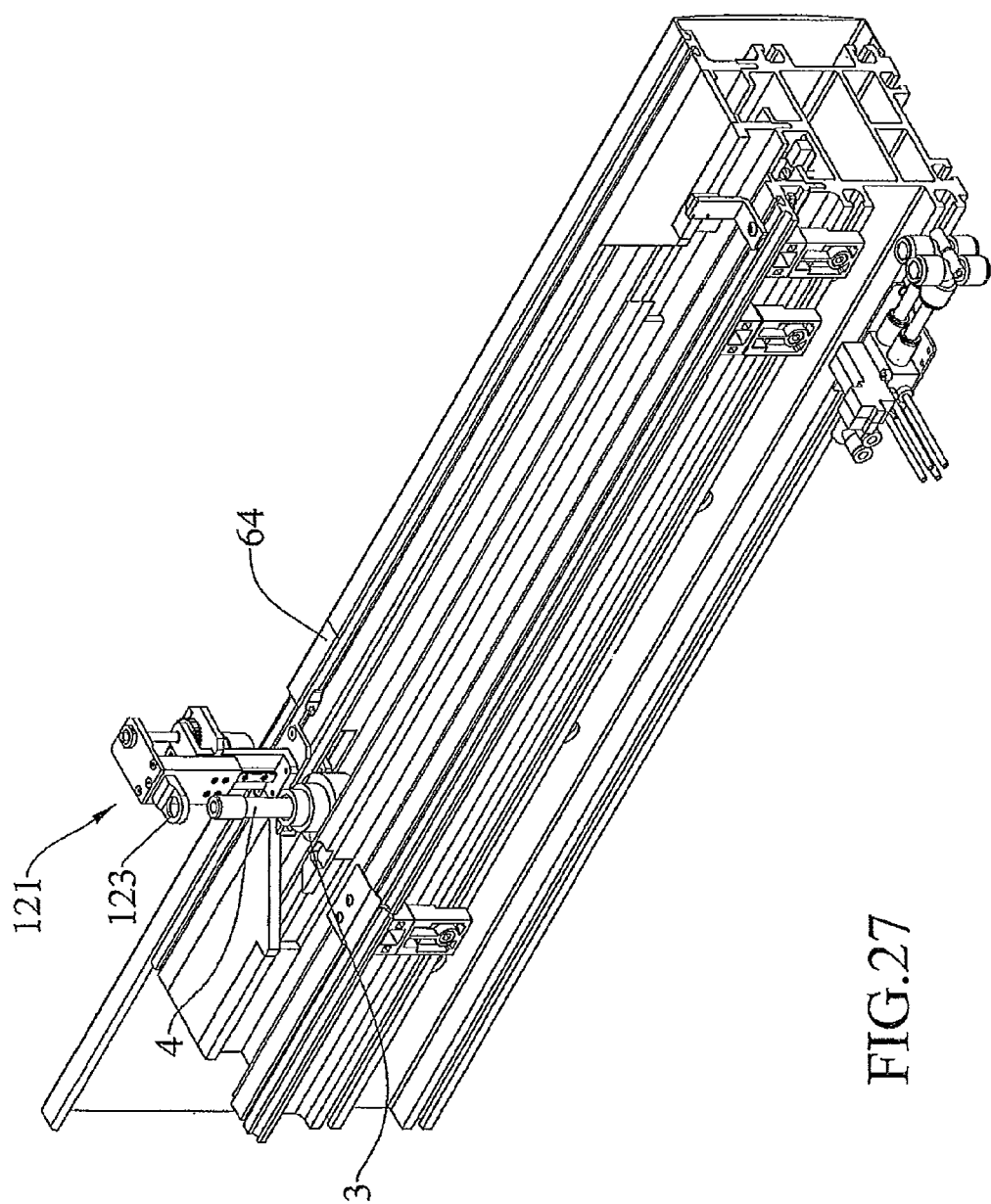
FIG. 27 shows a perspective view of a system portion comprising a device for blocking the test tube in a sampling position, in resting position.

Such a ring 122, controlled by a pneumatic piston, or alternatively, by an electric motor is vertically movable between a high rest position (FIG. 27) and a lower blocked position, when the test tube is stopped in the working point, before sampling, so that the ring 122 applies a minor pressure about the cap of the test tube.

During the sampling, the needle is inserted in the test tube penetrating the rubber of the plug and then exiting after having performed the aspiration.

In virtue of the presence of the ring 123, the test tube, despite being stressed in the vertical direction, remains blocked in the carrier without moving, thus allowing the mechanical arm of the tester to extract the needle from the rubber of the cap. At the end of the process, the block 122 returns to high position allowing the test tube to proceed in its path.

In conditions of high loads of test tubes to be processed, a carrier flow adjusting module 81 (FIG. 24), having the function of conveying carriers 3 loaded with test tubes 4 to parking lanes waiting for the excessive traffic to be processed by the system, may be present.

Figure 24:
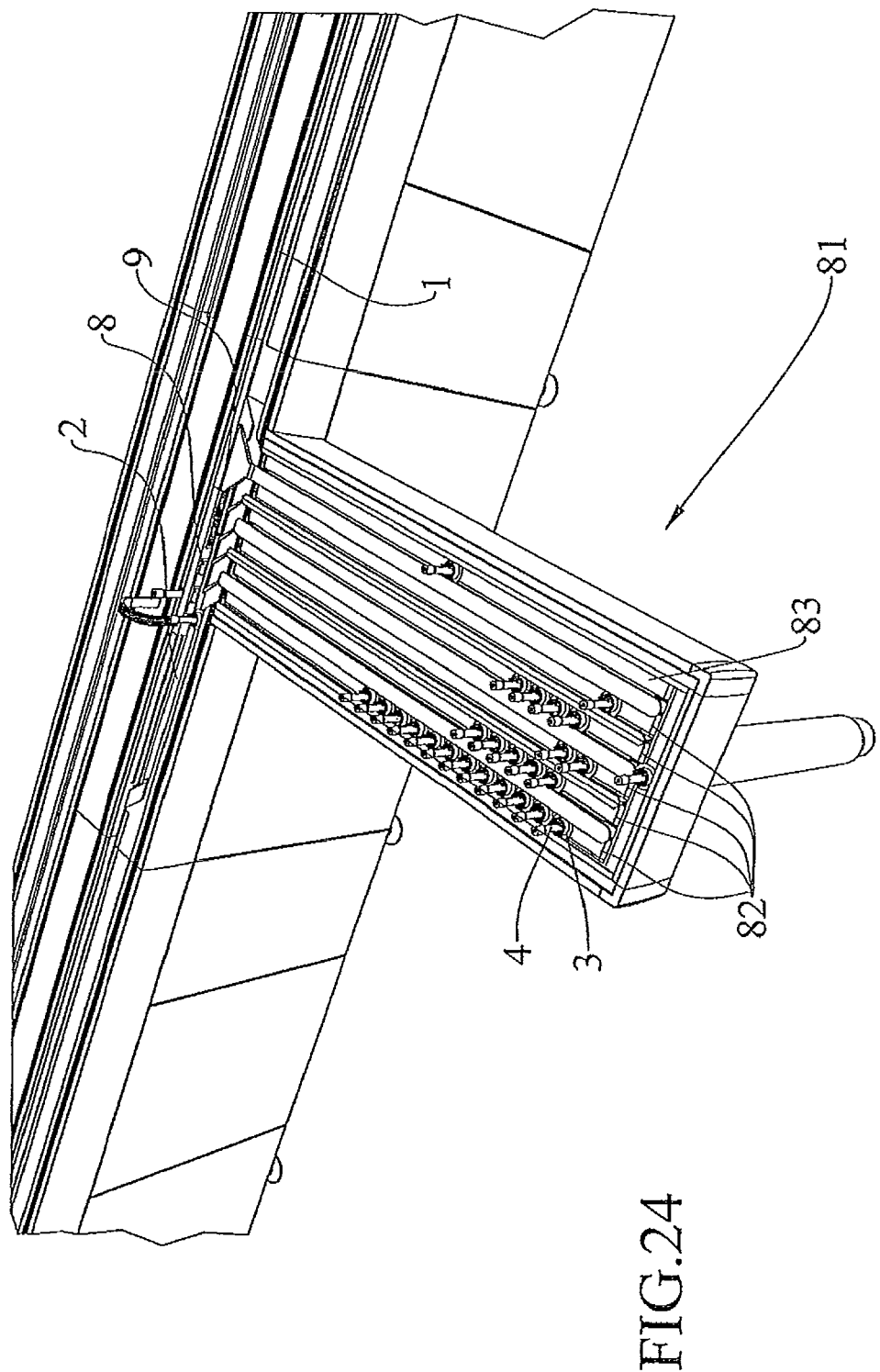
FIG. 24 is a perspective view of a portion of the system comprising a module adapted to adjust the flow of carriers.

In detail, the control unit 100, according to the processing performed on the test tubes, may decide to divert the carriers loaded into said flow adjusting module 81. Such a choice is determined on the basis of the load of the pre-testing and testing modules: if a test tube 4 in a carrier 3 must be processed by a given module at that time working for processing other test tubes, it is put on hold in the flow adjusting module 81. Said flow adjusting module 81 consists of five parking lanes 82 adapted to accommodate test tubes 4 in the carriers 3. Such test tubes are released onto the main conveying lane 1 by means of the releasing lane 83. The conveying and releasing flow of the carriers 3 in the flow adjusting module 81 is adjusted by the presence of the carrier diverting devices 9 and stop gates 8 located on the secondary lane 2, as shown in FIG. 24.

The invention claimed is:

1. An automated laboratory system for handling test tubes containing biological material specimens supported by conveying devices along guide lanes, in which motorized conveyor bells run,
 wherein it comprises modules which are mutually assembled in a variable number according to different configurations,
 each module comprising a main lane and at least a secondary lane parallel with said main lane, and communicating with each other by a diverting linear device which comprises a front support and a rear support which fix the diverting device to the structure of the main lane, flow governors adapted to adjust the movement of a cylinder responsible for the rotation of a lever about a pin between a resting position adapted to allow the conveying device to proceed its travel in the main lane, and a working position adapted to linearly divert the conveying device from the main lane to the secondary lane,
 wherein it includes a lifting device of the conveying belt adapted to avoid the contact between the belt and the supporting structure of the lanes in case of a compressing action on the test tube and therefore on the belt.

2. A system according to claim 1, wherein said lifting device comprises an external body containing a pneumatic cylinder fed by means of a flow governor adapted to allow the rotation of a runner about a pin integral with said external body between a resting position and a working position with the raised belt, a spring inside the runner allowing the return of the same to the resting position.

3. A system according to claim 1, wherein it includes modules composable according to various configurations, each of which comprises a first couple of adjacent and reciprocally parallel main and secondary lanes for overtaking the conveying devices and/or for addressing the conveying devices of the test tubes to the pre-testing, testing and post-testing stations, for sliding the conveying devices by means of corresponding conveying belts accommodated in said lanes, movable in the same direction, and a second couple of similar lanes, parallel and adjacent to said first couple, but with an opposite direction of movement of the conveyor belts with respect to said first pair.

4. A system according to claim 1, wherein it comprises a photo-video presence and height detecting device comprising two photoelectric sensors activated by the control unit when an antenna positioned close to a detecting point detects an identification code of the conveying device, the first a first sensor being activated for sensing the presence of the test tube in the conveying device, a second sensor being activated for sensing the height of the test tube, the presence of the test tube activating the barcode reader for a barcode present on the label of the test tube.

5. A system according to claim 1, wherein it comprises a corner portion consisting of two adjacent, rectilinear conveying modules, the passage of the test tubes from one module to the other being determined by motorized horizontal plates adapted to take the conveying device of the test tube from a belt of the first module thus depositing it on the belt of the second module.

6. A system according to claim 5, wherein it comprises two rectilinear conveying modules being integral with one another and having a "T" shape.

7. A system according to claim 1, wherein said conveying devices comprise transponders powered by an electromagnetic field generated by a network of antennas.

8. A system according to claim 1, wherein it comprises an adjusting module of the flow of loaded carriers having parking lanes and a releasing lane.

9. A system according to claim 1, wherein it comprises a U-turn device in an intermediate segment of the conveying system, comprising a U-turn plate on which the carriers are conveyed by means of the main lane, the secondary lane providing for diverting the carrier if the U-turn is not required.

10. An automated laboratory system for handling test tubes containing biological material specimens supported by conveying devices along guide lanes, in which motorized conveyor belts run,
 wherein it comprises modules which are mutually assembled in a variable number according to different configurations,
 each module comprising a main lane and at least a secondary lane parallel with said main lane, and communicating with each other by a diverting linear device which comprises a front support and a rear support which fix the diverting device to the structure of the main lane, flow governors adapted to adjust the movement of a cylinder responsible for the rotation of a lever about a pin between a resting position adapted to allow the conveying device to proceed its travel in the main lane, and a working position adapted to linearly divert the conveying device from the main lane to the secondary lane,
 wherein it comprises stop gates each of which comprises an external body fixed to the structure of the conveying module by means of a support, and enclosing a movable selector by means of a pneumatic cylinder, fed by a flow governor, between a blocking position of the conveying device and a resting position in which the passage of the conveying device is allowed, a spring located inside the selector allowing the return to the resting position from the blocking position.

11. An automated laboratory system for handling test tubes containing biological material specimens supported by conveying devices along guide lanes, in which motorized conveyor belts run,
 wherein it comprises modules which are mutually assembled in a variable number according to different configurations,
 each module comprising a main lane and at least a secondary lane parallel with said main lane, and communicating with each other by a diverting linear device which comprises a front support and a rear support which fix the diverting device to the structure of the main lane, flow governors adapted to adjust the movement of a cylinder responsible for the rotation of a lever about a pin between a resting position adapted to allow the conveying device to proceed its travel in the main lane, and a working position adapted to linearly divert the conveying device from the main lane to the secondary lane,
 wherein it comprises a test tube blocking device which includes a ring vertically and selectively movable between a high resting position and a low blocking position of the test tube in which the ring is coupled with the test tube cap.

* * * * *